United States Patent
Leonardi et al.

(10) Patent No.: US 6,271,234 B1
(45) Date of Patent: Aug. 7, 2001

(54) 1,4-DISUBSTITUTED PIPERAZINES

(75) Inventors: Amedeo Leonardi, Milan; Gianni Motta, Barlassina; Carlo Riva, Varese; Luciano Guarneri, Garbagnate; Elena Poggesi, Milan, all of (IT)

(73) Assignee: Recordati S.A., Chemical and Pharmaceutical Company, Chiasso (CH)

( * ) Notice: Subject to any disclaimer, the term of this patent is extended or adjusted under 35 U.S.C. 154(b) by 0 days.

(21) Appl. No.: 09/266,534

(22) Filed: Mar. 11, 1999

Related U.S. Application Data

(63) Continuation-in-part of application No. 09/127,058, filed on Jul. 31, 1998, now abandoned.
(60) Provisional application No. 60/070,266, filed on Dec. 31, 1997, and provisional application No. 60/070,267, filed on Dec. 31, 1997.

(30) Foreign Application Priority Data

Aug. 1, 1997 (IT) ................................. MI97A1862
Aug. 1, 1997 (IT) ................................. MI97A1863

(51) Int. Cl.$^7$ ........................ A61K 31/496; C07D 401/12
(52) U.S. Cl. ........................ 514/253.01; 544/360
(58) Field of Search .......................... 514/235.8, 252, 514/255, 253.01; 544/359, 360

(56) References Cited

U.S. PATENT DOCUMENTS

| | | | |
|---|---|---|---|
| 5,827,847 | * 10/1998 | Cliffe et al. | 514/212 |
| 5,990,114 | * 11/1999 | Leonardi et al. | 514/255 |

FOREIGN PATENT DOCUMENTS

| | | |
|---|---|---|
| 512755 | * 11/1992 | (EP) . |
| 0711757 | 5/1996 | (EP) . |
| 0748800 | 12/1996 | (EP) . |
| 2255337 | 4/1992 | (GB) . |
| 10-77271 | * 3/1998 | (JP) . |
| WO 94/21610 | 9/1994 | (WO) . |
| 94/09780 | * 11/1994 | (WO) . |
| WO 95/04049 | 2/1995 | (WO) . |
| WO 95/17831 | 7/1995 | (WO) . |
| 95/33725 | * 12/1995 | (WO) . |
| WO 95/33743 | 12/1995 | (WO) . |
| WO 96/14846 | 5/1996 | (WO) . |
| 97/03982 | * 2/1997 | (WO) . |
| WO 99/06382 | 2/1999 | (WO) . |

OTHER PUBLICATIONS

Chemical Abstract for JP 1077,271, vol. 128, No. 294706 (Takahashi et al), 1998.*
Albertson N.F., Org. React., 12:189–197, 1962.
Albertson N.F., Org. React., 12:205–218, 1962.
Andersson K.–E., Drugs, 35:477, 1988.
Baldwin J.E., et al., J. Org. Chem., 47:1385,1982.
Bliss C.I., Quart. J. Pharm Pharmacol., 11:192, 1938.
Cramer R., et al., J. Org. Chem., 40:2267, 1975.
De Groat, W.C., Neurobiol. of Incontinence, Ciba Found. Symp., 151:27, 1990.
Doherty, A.M., et al., J. Med. Chem., 35:2, 1992.
Doleschall, G., et al., Tetrahedron, 32:57, 1976.
Dray, A., J. Pharmacol. Methods, 13:157, 1985.
Fargin, A., et al., Nature, 335:358–360, 1988.
Greene, T.W., Protective Groups in Organic Synthesis, Wiley, pp. 218–287, 1981.
Guarneri, L., et al., Drugs of Today, 30:91, 1994.
Guarneri, L., Pharmacol. Res., 27:173, 1993.
Ishihara, Y., Chem. Pharm. Bull., 39:3236, 1991.
Jacobi, K.–R. Chem. Ber., 113, 1933.
Johnson, M.R., and Rickbourn B., J. Org. Chem., 35:1041, 1970.
Kaye, I.A.., J. Am. Chem. Soc., 73:5467, 1951.
Khuthier, A.–H., et al., J. Org. Chem., 52:1710, 1987.
Lepor, H., Urology, 42:483, 1993.
Lindley, J., Tetrahedron, 40:1433, 1984.
Louie J., et al., J. Org Chem., 62:1268, 1997.
Maggi, C.A.., et al., Brain Res., 380:83, 1986.
Maggi, C.A.., et al., J. Pharmacol Exp. Ther., 230:500, 1984.
Marcoux, J–R. et al., J. Org. Chem., 62:1568, 1997.
Martin, G.E. et al., J. Med Chem., 32:1052, 1989.
McGuire E. J., Campbell's Urology 5$^{th}$ Ed., 616–638, 1986.
Nutaitus, C.F. and Gribble, N., Tetrahedron Lett., 24:4287, 1983.
Ranu, B. and Chakraborty R., Tetrahedron Lett., 31:7663, 1990.
Ratouis, R., et al., J. Med. Chem., 8:104, 1965.
Ruffman, R. et al., J. Int. Med Res., 16:317, 1988.
S.N., Synlett, Note 12:328, 1996.
Wolfe, J.P. et al., J. Org. Chem., 62:1264, 1997.

* cited by examiner

*Primary Examiner*—Emily Bernhardt
(74) *Attorney, Agent, or Firm*—Darby & Darby

(57) ABSTRACT

Disclosed herein are novel compounds and methods for the treatment of disorders of the lower urinary tract. The novel compounds are 1,4-disubstituted piperazine derivatives. The methods comprise the administration of the novel compounds of the invention, and other compounds that bind to 5HT$_{1A}$ receptors, for treating disorders of the lower urinary tract.

17 Claims, No Drawings

1,4-DISUBSTITUTED PIPERAZINES

RELATED APPLICATIONS

This is a continuation-in-part of Ser. No. 09/127,058, filed Jul. 31, 1998, now abandoned which claims priority under 35 U.S.C. §119 from U.S. provisional applications Ser. Nos. 60/070,266 and 60/070,267 both filed Dec. 31, 1997 and Italian patent applications MI97A 001862 and MI97A 001863, all of which are incorporated by reference herein in their entirety

FIELD OF THE INVENTION

This invention relates to novel 1,4-disubstituted piperazines that bind to serotonergic receptors, to pharmaceutical compositions containing them, and to uses for such derivatives and compositions.

BACKGROUND OF THE INVENTION

In mammals, micturition (urination) is a complex process that requires the integrated actions of the bladder, its internal and external sphincters, the musculature of the pelvic floor, and neurological control over these muscles at three levels (in the bladder wall or sphincter itself, in the autonomic centers of the spinal cord, and in the central nervous system at the level of the pontine micturition center (PMC) in the brainstem (Pons) under the control of cerebral cortex) (De Groat, *Neurobiology of Incontinence*, (Ciba Foundation Symposium 151:27, 1990). Micturition results from contraction of the detrusor muscle, which consists of interlacing smooth muscle fibers under parasympathetic autonomic control from the sacral spinal cord. A simple voiding reflex is formed by sensory nerves for pain, temperature, and distension that run from the bladder to the sacral cord. However, sensory tracts from the bladder also reach the PMC, resulting in the generation of nerve impulses that normally suppress the sacral spinal reflex arc controlling bladder emptying. Thus, normal micturition is initiated by voluntary suppression of cortical inhibition of the reflex arc and by relaxation of the muscles of the pelvic floor and the external sphincter. Finally, the detrusor muscle contracts and voiding occurs.

Abnormalities of lower urinary tract function, e.g., dysuria, incontinence, and enuresis, are common in the general population. Dysuria includes urinary frequency, nocturia, and urgency, and may be caused by cystitis, prostatitis or benign prostatic hypertrophy (BPH) (which affects about 70% of elderly males), or by neurological disorders. Incontinence syndromes include stress incontinence, urgency incontinence, and overflow incontinence. Enuresis refers to the involuntary passage of urine at night or during sleep.

Prior to the work of the present inventors, treatment of neuromuscular dysfunction of the lower urinary tract has involved administration of compounds that act directly on the bladder muscles, such as flavoxate, a spasmolytic drug (Ruffman, *J. Int.Med.Res.* 16:317, 1988) also active on the PMC (Guarneri et al., *Drugs of Today* 30:91, 1994), or anticholinergic compounds such as oxybutynin (Andersson, *Drugs* 35:477, 1988). The use of α1-adrenergic receptor antagonists for the treatment of BPH is also common but is based on a different mechanism of action. (Lepor, *Urology*, 42:483, 1993).

However, treatments that involve direct inhibition of the pelvic musculature (including the detrusor muscle) may have unwanted side effects such as incomplete voiding or accommodation paralysis, tachycardia and dry mouth (Andersson, *Drugs* 35:477, 1988). Thus, it would be preferable to utilize compounds that act via the peripheral or central nervous system to, for example, affect the sacral spinal reflex arc and/or the PMC inhibition pathways in a manner that restores normal functioning of the micturition mechanism. N-(2-pyridyl)-N,2-[4-(2-methoxyphenyl)-1-piperazinyl]ethylcyclohexanecarboxamide (compound A, below) is described in GB 2255 337 A and is reported to possess 5-HT$_{1A}$ antagonistic properties. It is also disclosed that it can be used for the treatment of central nervous system disorders, for example as an anxiolytic agent in the treatment of anxiety.

(A)

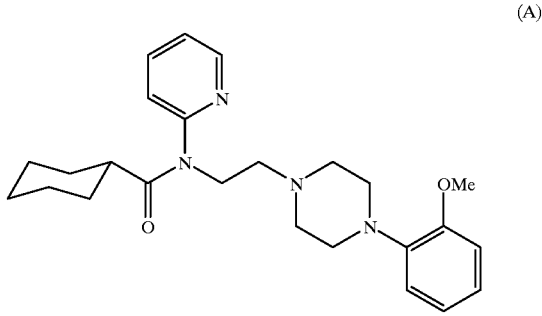

The compounds of the present invention, described below, are structurally different from compound A because of the novel substitutions on the aromatic ring bound to the piperazine moiety and because of the insertion of a series of spacer moieties (Z) between the piperazine and phenyl rings. These structural variations are not disclosed by GB 2255337 A, particularly with regard to compounds that can be used to improve urinary tract function. These novel compounds also have a longer duration of action than does compound A in pharmacological tests predictive of activity on the lower urinary tract. This is especially true with respect to the activity of the compounds of the invention against urinary incontinence, which is a novel therapeutic indication for this class of compounds acting at the 5-HT$_{1A}$ receptor.

SUMMARY OF THE INVENTION

In one aspect, the invention is directed to compounds of formula I:

(I)

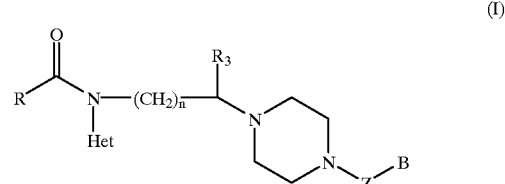

wherein
  n is 1 or 2,
  Het is a monocyclic heteroaryl radical,
  R is a cycloalkyl or a monocyclic heteroaryl radical,
  R$_3$ is a hydrogen atom or a lower alkyl group,
  Z is a bond, —CH$_2$—, —CH$_2$CH$_2$—, —CH$_2$C(O)—, —CH$_2$CH(OH)—, —O—, —OCH$_2$— or —C(O)— each of which is depicted with left end being the end which attaches to the piperazine ring and the right end being the end which attaches to group B, wherein B is selected from the group consisting of a heteroaryl radical, an unsubstituted aryl radical, and a substituted aryl radical, where the substituted aryl radical is represented by the following formula:

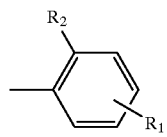

where $R_1$ is a single substituent selected from the group consisting of hydrogen, alkoxy, halogen, nitro, amino, acylamino, alkylamino, dialyklamino and alkylsulfonylamino, and $R_2$ is selected from the group consisting of an alkoxy, polyfluoroalkoxy, cyano, halogen and aminocarbonyl radical, and where the heteroaryl radical is selected from the group consisting of a mono or a bicyclic aromatic radical comprising from 5 to 12 ring atoms, where one or more of the ring atoms are selected from the group consisting of nitrogen, oxygen, and sulfur; with the proviso that when the compound of formula I has the formula

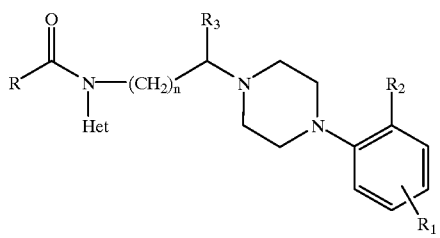

then $R_2$ is not halogen when $R_1$ is H, and $R_2$ is not alkoxy, cyano, or aminocarbonyl when $R_1$ is hydrogen, halogen, nitro or amino.

The invention also includes the enantiomers, diastereomers, N-oxides, crystalline forms, hydrates and pharmaceutically acceptable salts of these compounds, as well as metabolites of these compounds having the same type of activity (hereafter sometimes referred to as "active metabolites").

The invention further provides pharmaceutical compositions comprising a compound of formula I or an enantiomer, diastereomer, N-oxide, crystalline form, hydrate or pharmaceutically acceptable salt of the compound, in admixture with a pharmaceutically acceptable diluent or carrier.

In another aspect, the present invention is directed to methods for reducing the frequency of bladder contractions due to bladder distension by administering one or more selected compounds of formula I to a mammal (including a human) in need of such treatment, in an amount or amounts effective for the particular use.

In a further aspect, the present invention is directed to methods for treating disorders of the urinary tract in a subject in need of such treatment, comprising administering an effective amount of a compound of formula 1 to ameliorate at least one of urinary urgency, increased urinary frequency, incontinence, urine leakage, enuresis, dysuria, urinary hesitancy, and difficulty in emptying bladder.

In yet another aspect, the invention is directed to methods for binding compounds to 5-$HT_{1A}$ serotonergic receptors, and, by virtue of this binding activity, to methods for the treatment of CNS disorders due to serotonergic dysfunction such as anxiety, depression, hypertension, sleep/wake cycle disorders, feeding behavior, sexual function and cognition disorders in mammals, particularly in humans, by delivering to the environment of the 5-$HT_{1A}$ serotonergic receptors, e.g., to the extracellular medium (or by administering to a mammal possessing such receptors) an effective amount of a compound of the invention.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The activity of the compounds of the invention as inhibitors of frequency of micturition renders them useful for the treatment of neuromuscular dysfunctions of the lower urinary tract in mammals, including without limitation dysuria, incontinence and enuresis.

Surprisingly, the introduction of selected substituents on the phenyl ring directly bound to the piperazine moiety of formula Ia and of the Z group in compounds of formula I impart to these compounds a distinctly longer duration of action than is possessed by compound A.

The unexpected properties of the compounds of the invention were found by comparing the behavior of compound A and compounds of the invention in a rat model. The rhythmic contraction of rat bladders was induced by filling the bladders with a physiologic solution. The effect of compounds of the invention on the frequency and amplitude of the contractions was evaluated. Of particular interest is the time of disappearance of induced contractions. The results are shown in Table 1 of Example 28.

The effect of the drugs currently available for administration to humans for treatment of neuromuscular function of the lower urinary tract (flavoxate and oxybutynin) on the above-described rat model is also shown, for comparative purposes, in Table 1.

The compounds of the invention acted for a longer period of time (as measured by duration of bladder quiescence with no contractions) than did compounds A, flavoxate, and oxybutynin. Moreover, in contrast to oxybutynin, the compounds of the invention did not affect the amplitude of the contractions, suggesting no impairment of bladder contractility.

Finally, the demonstration that the compounds of the invention have a high affinity for the 5-$HT_{1A}$ receptor (Example 29, Table 2) suggests a role for this receptor in the action of the compounds of the invention.

The pharmacological tests (and Tables) described above are described in more detail in the Examples below.

As used herein with reference to variable R of compound I, cycloalkyl radicals include $C_5$–$C_7$ cycloalkyls; with reference to variables R and Het, monocyclic heteroaryl radicals include monocyclic aromatic radicals that contains 5 to 7 ring atoms, and that contains one or more hetero atoms (e.g. oxygen, nitrogen, or sulfur). Lower alkyl, as used herein, includes $C_1$ to $C_6$ alkyl. Alkyl, when used in, for example "alkylsulfonylamino", also means lower alkyl, preferably $C_1$ to $C_6$ alkyl.

With reference to variable B, substituted aryl is represented by the following group:

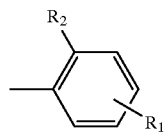

where $R_1$ is a single substituent selected from the group consisting of hydrogen, alkoxy, halogen, nitro, amino, acylamino, alkylamino, dialyklamino and alkylsulfonylamino, R is an alkoxy, polyfluoroalkoxy, cyano, halogen or aminocarbonyl radical.

With reference to variable B, heteroaryl radical includes a mono or bicyclic aromatic radical containing one or more heteroatoms (e.g. nitrogen, oxygen, sulfur), which contain from 5 to 12 ring atoms.

It is preferred that R be a cycloalky group, most preferably a $C_6$ or $C_7$ cycloalkyl group. It is preferred that $R_3$ be hydrogen or methyl. It is preferred that variable $R_2$ is a trifluoroalkoxy group, most preferably 2,2,2-trifluoroethoxy. Preferred substituents at variable $R_1$ are hydrogen, halogen, or acylamino. If $R_1$ is a halogen, it is most preferably fluorine or chlorine. If $R_1$ is acylamino, it is most preferably acetylamino. It is preferred that Z is bond or $CH_2$. A preferred value for n is 1. A preferred substituent at variable Het is pyridyl.

Subjects who can benefit from administration of the compounds and compositions of the invention include humans who are affected by neuromuscular dysfunction of the lower urinary tract, described by E. J. McGuire in "Campbell's UROLOGY" $5^{th}$ Ed. 616–638, 1986, W. B. Saunders Company, and also include patients affected by any physiological dysfunction related to impairment of $5\text{-HT}_{1A}$ receptor function. Such dysfunctions include, without limitation, central nervous system disorders such as depression, anxiety, eating disorders, sexual dysfunction, addiction, and related problems.

The present invention encompasses pharmaceutical formulations comprising the compounds disclosed above, as well as methods employing these formulations for treating neuromuscular dysfunction of the lower urinary tract such as dysuria, incontinence, enuresis, and the like. Dysuria includes urinary frequency, nocturia, urgency, and difficulty in emptying the bladder, i.e., a suboptimal volume of urine is expelled during micturition.

Incontinence syndromes include stress incontinence, urgency incontinence, and overflow incontinence. Enuresis refers to the involuntary passage of urine at night or during sleep.

Without wishing to be bound by theory, it is believed that administration of $5\text{-HT}_{1A}$ receptor antagonists prevents unwanted activity of the sacral reflex arc and/or cortical mechanisms that control micturition. Thus it is contemplated that a wide range of neuromuscular dysfunctions of the lower urinary tract can be treated using the compounds of the present invention.

An "effective amount" of the compound for treating a urinary disorder is an amount that results in measurable amelioration of at least one symptom or parameter of the disorders described above.

An effective amount for treating the disorder can easily be determined by empirical methods known to those of ordinary skill in the art, such as by establishing a matrix of dosages and frequencies of administration and comparing a group of experimental units or subjects to each point in the matrix. The exact amount to be administered to a patient will vary depending on the state and severity of the disorder and the physical condition of the patient. A measurable amelioration of any symptom or parameter can be determined by a physician skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination, either or both of which may be reduced using the methods of the present invention. In the case of incontinence, any reduction in the frequency or volume of unwanted passage of urine is considered a beneficial effect of the present methods of treatment.

The compounds of the present invention may be formulated into liquid dosage forms with a physiologically acceptable carrier, such as, for example, phosphate buffered saline or deionized water. The pharmaceutical formulation may also contain excipients, including preservatives and stabilizers, that are well-known in the art. The compounds can be formulated into solid oral or non-oral dosage units such as, for example, tablets, capsules, powders, and suppositories, and may additionally include excipients, including without limitation lubricant(s), plasticizer(s), colorant(s), absorption enhancer(s), bactericide(s), and the like.

Modes of administration include oral and enteral, intravenous, intramuscular, subcutaneous, transdermal, transmucosal (including rectal and buccal), and by-inhalation routes. Preferably, an oral or transdermal route is used (i.e., via solid or liquid oral formulations, or skin patches, respectively).

The amount of the agent to be administered can range from between about 0.01 and about 25 mg/kg/day, preferably from between about 0.1 and about 10 mg/kg/day and most preferably from between about 0.2 and about 5 mg/kg/day. It will be understood that the pharmaceutical formulations of the present invention need not in themselves contain the entire amount of the agent that is effective in treating the disorder, as such effective amounts can be reached by administration of a plurality of doses of such pharmaceutical formulations.

In a preferred embodiment of the present invention, compounds are formulated in capsules or tablets, each preferably containing 50–200 mg of the compounds of the invention, and are most preferably administered to a patient at a total daily dose of 50–400 mg, preferably 150–250 mg, and most preferably about 200 mg for relief of urinary incontinence and dysfunctions amenable to treatment with $5\text{-HT}_{1A}$ receptor ligands.

The methods, tables and examples provided below are intended to more fully describe preferred embodiments of the invention and to demonstrate its advantages and applicability, without in any way limiting the scope of the invention.

SYNTHESIS OF THE COMPOUNDS OF THE INVENTION

The compounds of the invention, i.e., compounds of formula (I), may generally be prepared as shown by Scheme 1 where Het, n, Z, B, $R_3$ have the same meanings as above:

Scheme 1

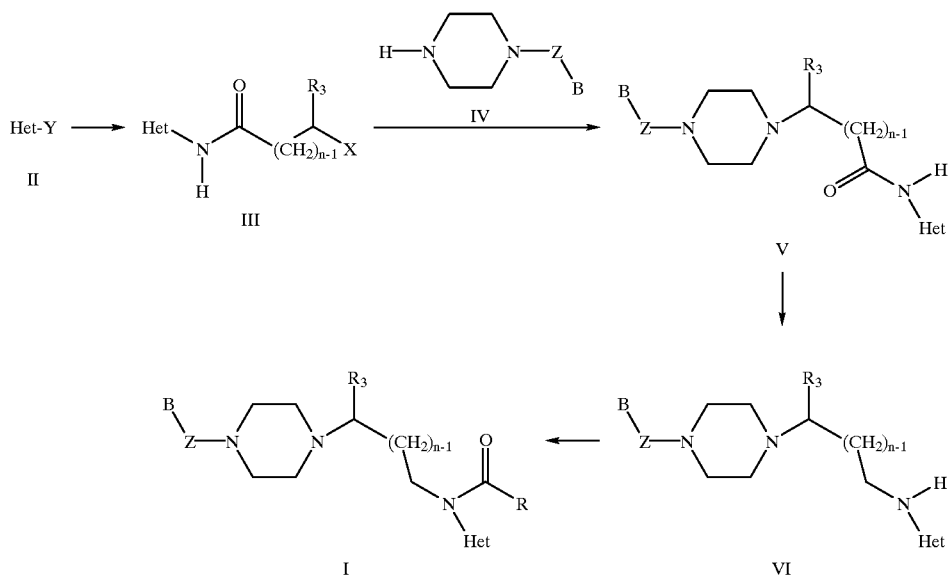

The amino-substituted heteroaromatic starting materials of formula II (Y=NH$_2$) are commercially available, or their syntheses are well-known to those of ordinary skill in the art. The intermediates of formula II can be converted into intermediates with formula III by conventional acylation procedures known to those skilled in the art, e.g., by using acylating reagents of the formula X—CH(R$_3$)—(CH$_2$)$_{n-1}$—C(O)—X$_1$, where X is a leaving group, e.g. Br, Cl, I, p-toluenesulfonyloxy, methanesulfonyloxy and X$_1$, for example, is Br, Cl, OH, and the like. Where n is 2, the acylating reagent can be an acryloyl acylating reagent, which affords the 2,3-unsaturated amides of formula Het-NH—C(O)—CH=CH—R$_3$.

Intermediates with formula III can be condensed by conventional methods with the piperazine derivatives IV, in the presence of a base, to afford intermediates with formula V.

An alternative method of preparing intermediates of formula V consists of acylating starting materials of formula II with compounds of the formula VII, below, where X$_1$, Z, B, R$_3$ and n are defined as set forth above:

VII

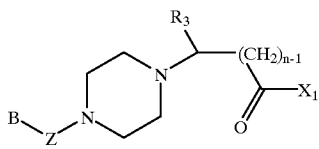

The acylation can be performed by conventional procedures, known to those of ordinary skill. For example, if X$_1$ of the acylating agent is OH, the amine-substituted heteroaromatic can be acylated by the addition of a coupling agent (e.g. diethyl cyanophosphonate, dicyclohexylcarbodiimide or N,N'-carbonyldiimidazole) optionally in the presence of a promoting agent (e.g. N-hydroxysuccinimide, 4-dimethylaminopyridine) in an aprotic or a chlorinated solvent (e.g. N,N-dimethylformamide, chloroform, methylene chloride) at −20° C./140° C. (Albertson, *Org. React.* 1962, 12, 205–218; Doherty et al., *J. Med. Chem* 1992, 35, 2; Staab et al., *Newer Methods Prep. Org. Chem.* 1968, 5, 61; Ishihara, *Chem. Pharm. Bull.* 1991,39,3236).

Other well-known reaction procedures for acylation of amines include the mixed anhydride method by reaction of intermediates with formula VII with an alkyl chloroformate in the presence of a tertiary amine (e.g. triethylamine) followed by addition of the heteroarylamine reagent reagent in an aprotic solvent (e.g. dioxane, methylene chloride), optionally in the presence of, e.g 1-hydroxypiperidine as a promoting agent (*Org. React.* 1962, 12, 157). If Xof the acylating agent is Cl or Br, intermediates with formula VII can be condensed with starting materials of formula II in an aprotic solvent (e.g chloroform, 1,2-dichloroethane, dimethylformamide, dioxane, toluene) in the presence of a base (e.g triethylamine, pyridine, 4-dimethylaminopyridine, potassium or cesium or sodium carbonate). Intermediates of formula VII can be synthesized from arylpiperazines and a compound of the formula X—CH(R$_3$)—(CH$_2$)$_{n-1}$—C(O)—X$_1$, where X is as defined above and Xis OH or OAlk (Alk preferably represents lower alkyl, e.g methyl or ethyl). Compounds of formula VII can also be synthesized from the piperazines IV and a compound of the formula R$_3$—CH=CH—C(O)—X$_1$. This alternative method of preparing Intermediates of formula V by acylating starting materials of formula II is useful also when Z is CHOHCH$_2$, if the OH group is previously protected by procedures which are well-known to those of ordinary skill in the art.

Scheme 2

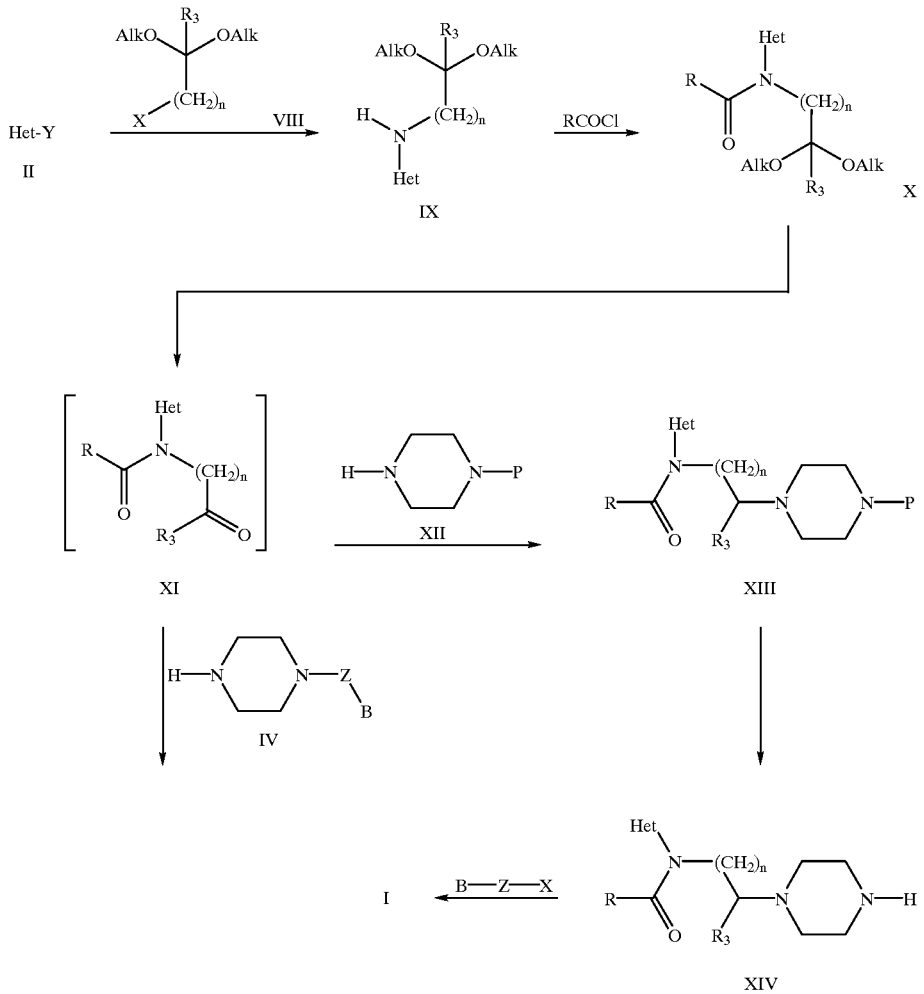

Intermediates with formula V can be then reduced to intermediates of formula VI by the use of reducing agents which can convert the amido functionality into an amino group. Such reducing agents include complex metal hydrides, e.g. lithium aluminum hydride in diethyl ether or tetrahydrofuran, or a stable diborane complex such as borane-tetrahydrofuran or borane-dimethyl sulfide, or the like (*J. Org. Chem* 1982, 47, 1389) used in a solvent suitable for reducing reactions, e.g. tetrahydrofuran. When Z is $CH_2C(O)$, these reduction procedures can in any case be applied if the keto group is previously protected by procedures which are well-known to those of ordinary skill in the art.

Subsequent acylation of intermediates of formula VI with R—C(O)Cl or other acylating reagents following conventional procedures (see above) results in compounds of the invention of formula I. Intermediates of formula VI can also be acylated as their azaanion, which can be produced by treatment of intermediates of formula VI with hard bases (e.g. sodium hydride, butyl lithium, lithium bis(trimethylsilyl)amide) in a suitable solvent (e.g. tetrahydrofuran, toluene, dioxane, 1,2-dimethoxyethane, diglyme). Another method to synthesize compounds of formula I, is depicted in Scheme 2 (above).

Heteroaryl compounds with formula II (Y=halogen) are used to alkylate protected aminoalkylaldehydes or aminoalkylketones respectively of formula VIII (X=$NH_2$) to give the corresponding acetals or ketals of heteroarylaminoalkylaldehydes or heteroarylamino alkylketones IX. The reaction can be carried out in a polar aprotic solvent such as pyridine, DMF, toluene, etc., at temperatures between +40° C. and +120° C., optionally in the presence of a base such as $Et_3N$.

An alternative reaction procedure to prepare intermediates of formula IX consists of alkylating heteroaryl compounds of formula II (Y=$NH_2$) with a protected compound of formula VIII (X=Br or other leaving group) by conventional procedures, or via an azaanion of compounds of formula II, obtained by the use of a strong base (e.g. n-butyl lithium, lithium diisopropylamide, lithium hexamethyldisilylamide, sodium hydride, sodium amide) in apolar or polar aprotic solvents (e.g. toluene, THF).

Intermediates of formula IX may be acylated with RCOCl to yield intermediates of formula X using the same acylation conditions described above (see Scheme 1). These intermediates are stable to normal laboratory conditions (i.e., light, humidity, temperature, etc.) and can be stored and deprotected by standard methods (e.g., acidic hydrolysis) just before their use in the following steps.

Carbonyl derivatives of formula XI, obtained from deprotection of compounds X, can be reacted with an appropriate N-substituted piperazine of formula IV under reductive amination conditions to give the compounds of the invention I. These reactions can be carried out in polar solvents such as methanol or ethanol, or chlorinated solvents such as dichloromethane or chloroform. Typically, alkali borohydrides such as $NaBH_4$, $NaBH_3CN$, and $NaBH(OAc)_3$ are employed as reducing agents. Additional, optional reaction components include acidic promoters such as acetic acid. The reactions proceed at temperatures between +10° C. and 100° C. When compounds with formula IV (Z=$CH_2$CO) are used, the reduction of a ketone to an alcohol functionality can be achieved with $NaBH_4$ as a reducing agent.

Alternatively, carbonyl compounds of formula XI may be reacted with an appropriate N-protected piperazine of formula XII, using the same reductive conditions described above, to give intermediates with structure XIII. The piperazinyl derivatives of formula XIV, obtained by deprotection of compounds with formula XIII by standard methods, can be alkylated with B—Z—X reagents (X=leaving group) or B—Z—CHO reagents (by standard reductive amination, see above), except when Z is O and $OCH_2$, to give the compounds of the invention I.

An alternative method to synthesize the compounds of formula I is depicted in scheme 3.

tions can be carried out in polar aprotic solvents such as N,N-dimethylformamide (DMF), tetrahydrofuran (THF), dioxane, acetone, acetonitrile or chlorinated solvents such as dichloromethane, or chloroform, at temperatures between 0° C. and 120° C. The reactions are typically performed in the presence of a proton acceptor such as triethylamine ($Et_3N$), diisopropylethylamine, and the like, and optionally in the presence of potassium iodide.

In the intermediates of formula XV, X and $X_1$ can be chloro, bromo, iodo, alkyl- or arylsulfonyloxy.

Another approach to the synthesis of intermediates of formula XVI utilizes compounds with formula II (Y=halogen, OTf) as starting materials. Het-Y is reacted with a suitable aminoalcohol of formula XV (X=$NH_2$, $X_1$=OH or protected OH) by direct nucleophilic displacement performed by conventional procedures known to those skilled in the art, usually in the presence of bases (e.g. diisopropylethylamine, sodium carbonate, lithium diisopropylamide, sodium tert-butoxide, etc.). One equivalent of excess reagent XV having X=$NH_2$ as proton acceptor is employed in the reaction, as described by G. Doleschall et al., Tetrahedron, 32, 57–64 (1976). These alkylation reactions can be carried out in an aprotic polar solvent such as DMF, toluene, and the like, or in a protic one such as

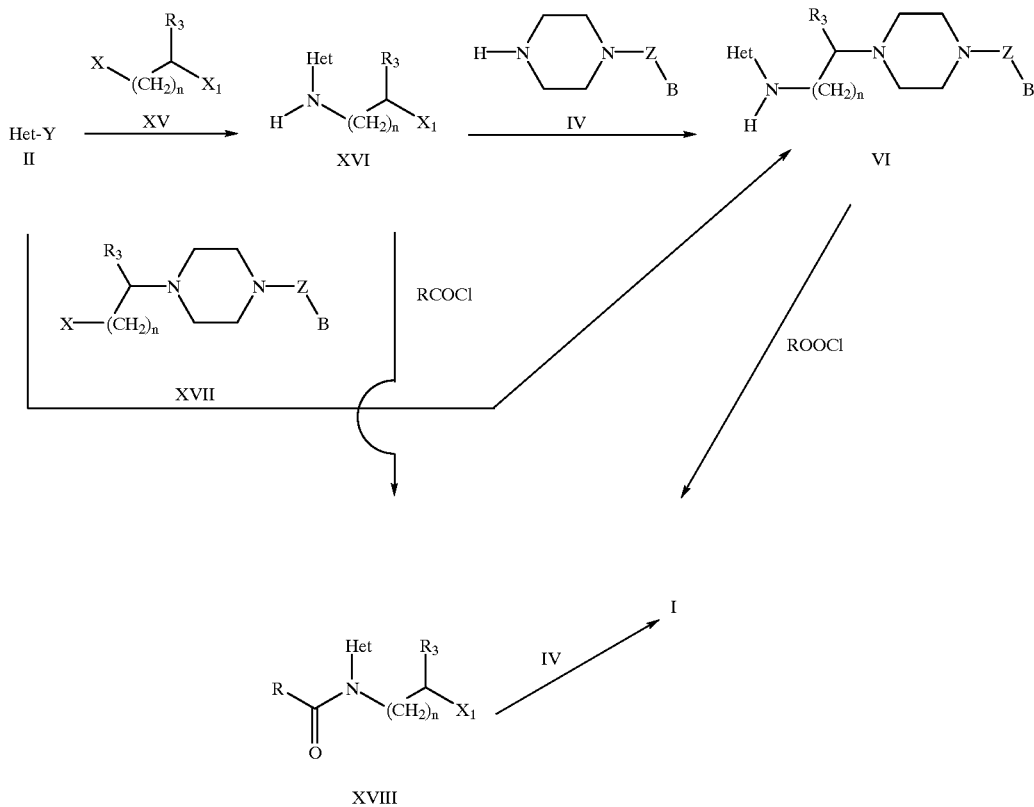

Scheme 3

The heteroarylamines of formula II (Y=$NH_2$) can be alkylated with an appropriate 1,ω-disubstituted alkane of formula XV to give an intermediate with formula XVI. Reacn-BuOH at temperatures between +40° C. and +140° C. The nucleophilic displacement can be obtained also via arylation of an azaanion of XV (with protected OH) obtained by the use of hard bases (e.g. sodium hydride, butyl lithium, lithium bis(trimethylsilyl)amide) in a suitable solvent (e.g. tetrahydrofuran, toluene, dioxane, 1,2-dimethoxyethane, diglyme). The nucleophilic displacement of the aminoalcohol XV on Het-Y (Y=hal, Otf) can also be performed in the presence of a metal catalyst that can be chosen among a large variety e.g. copper metal, copper (I) iodide or bromide or oxide (*Tetrahedron*, 1984, 40, 1433), nickel catalysts (*J. Org. Chem.*, 1975, 40, 2267) palladium dichloride, palladium diacetate, palladium tetrakis, bis(diphenylphosphine) palladium dichloride, palladium dibenzylidene acetone, bis (diphenylphosphinoferrocene) palladium dichloride (*Synlett*, 1996, 329; *J. Org. Chem.*, 1997, 62, 1568; 1997, 62, 1268; 1997, 62, 1264). The reactions can be performed at between room temperature and the reflux temperature of the solvent (e.g. dimethylacetamide, dimethylformamide, dioxane, acetonitrile, toluene, tetrahydrofuran) with or without a phosphine ligand (e.g. triphenyl phosphine or tri-o-tolylphosphine or bis(diphenylphosphino)ferrocene or 2,2'-bis(diphenylphosphino)-1,1'-binaphthyl or other commercially available phosphine ligands).

Aminoalcohols XVI ($X_1$=OH) are reacted with an halogenating agent such as $POCl_3$, $SOCl_2$, $PCl_5$ or $PBr_3$ to give intermediates of formula XVI ($X_1$=Cl, Br). These reactions are typically carried out in an aprotic solvent such as chloroform, DMF, or pyridine at temperatures between +50° C. and the reflux temperature of the solvent. These intermediates are used in the alkylation of an appropriate piperazine derivative with formula IV, to give intermediates of formula VI. These alkylations may be carried out in a chlorinated solvent such as dichloromethane, chloroform or 1,2-dichloroethane, or in a polar aprotic solvent such as DMF, THF, acetone, acetonitrile, n-butanol, etc., or in an apolar solvent such as toluene, benzene, n-heptane, and the like, at temperatures between 0° C. and 120° C. The reaction mixture can, optionally, contain a proton acceptor such as $Et_3N$, 4-dimethylaminopyridine, potassium carbonate, cesium carbonate, and the like. The reaction can also optionally be performed in the presence of potassium iodide.

Intermediates with formula VI may be also obtained by the alkylation reaction of compounds of formula II (Y=NH$_2$) with derivatives of formula XVII, in which B, $R_3$, Z, X and n have the same meanings as defined above. Such reactions may be carried out at the melting temperature of the reactants without solvent, or in an aprotic solvent such as dichloromethane, chloroform, DMF, THF, acetone, acetonitrile, or a protic one such as n-butanol, and the like at temperatures between 0° C. and +160° C. The reactions can, optionally, be performed in the presence of a proton acceptor, such as $Et_3N$, potassium or cesium carbonate, 4-dimethylaminopyridine; another optional reactant is potassium iodide. Additionally, intermediates of formula VI may be prepared by nucleophilic displacement of a compound of formula XVII (X=NH$_2$) on a compound of formula II (Y=Hal, OTf) by the methods discussed above for the preparation of XVI ($X_1$=OH).

Intermediates of formula VI can be acylated with suitable acyl chlorides to give compounds of formula I as described above An additional procedure to afford compounds of formula I is acylation of compounds XVI by conventional procedure to give compounds XVIII ($X_1$=leaving group), which can be finally reacted with the proper piperazine derivatives IV.

Intermediates with formulas IV and/or VI or XVII in which Z=CH$_2$CH(OH) are obtained from the same intermediates in which Z=CH$_2$C(O) by reduction. The reduction of carbonyl groups to alcohols may be carried out using metal hydrides such as LiAlH$_4$ (Rickborn J., J. Org. Chem. 35, 1041 (1970)), NaBH$_4$, Na(OAc)$_3$BH (Gribble N., Tetrahedron Lett. 24, 4287 (1983)), Zn(BH$_4$)$_2$ (Chakraborty R., Tetrahedron Lett. 31, 7663 (1990)) and the like as reducing agents. Diethyl ether, THF, methanol, ethanol, dioxane and solvent mixtures thereof that are suitable for use with strong bases and reducing agents may be used as reaction solvents, at temperatures between +10° C. and the reflux temperature of the solvent.

Alternatively, these reductions may be carried out to achieve compounds of formula I where Z is CH$_2$C(O) by employing lithium tri-t-butoxyaluminum hydride (Endy L., J. Org. Chem. 35, 549 (1970)) or other selective reducing agents.

The compounds of formula I where Z is O or OCH$_2$ and B is aryl may be prepared from the corresponding N-oxide derivatives of compounds I in which Z is a bond or CH$_2$ by thermal rearrangement (Meisenheimer isomerization):

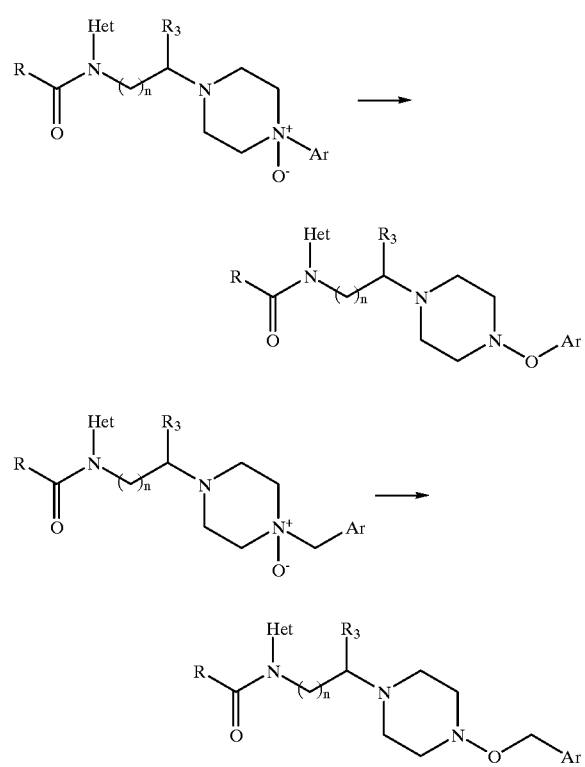

This reaction can be carried out in a polar aprotic solvent such as dioxane (Khuthier A. H. et al., J. Org. Chem. 52, 1710–1713 (1987) and references cited herein), at temperatures between 60° C. and the reflux temperature of the solvent.

Another method to synthesize compounds of formula I is depicted in scheme 4, below.

Scheme 4

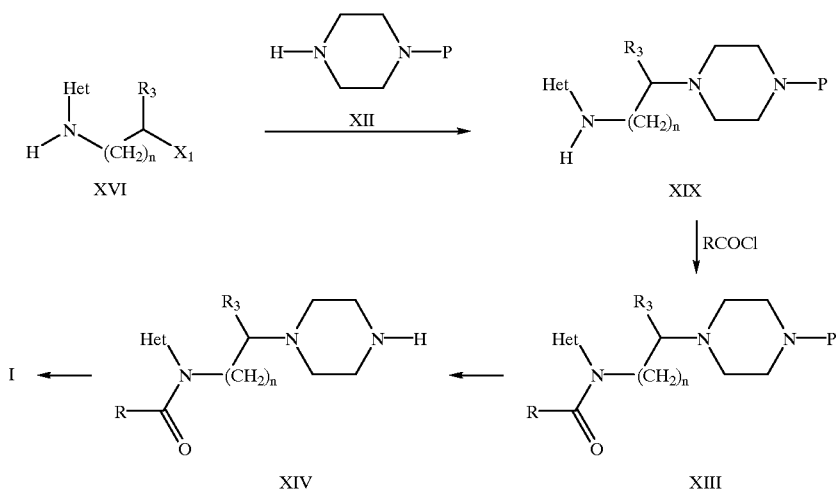

Intermediates of formula XVI, obtained as described in Scheme 3, may be used to alkylate mono-protected piperazines of formula XII, where P is t-butoxycarbonyl or benzyloxycarbonyl or other suitable protecting group, to afford intermediates with formula XIX. Several examples of protection and deprotection for various reactive groups can be found in: T. W. Greene, "Protective Groups in Organic Synthesis" Wiley Interscience (1991).

The reaction conditions for the preparation of intermediates of formula XIX are the same as described above in scheme 3.

Acylation of intermediates of formula XIX en route to the synthesis of intermediates with formula XIII (Scheme 2) can be performed under the same conditions employed for the synthesis of final compounds I in scheme 1.

Another method for the synthesis of intermediates with formula VI consists of alkylating the appropriate arylpiperazines with intermediates of formula XX, whose synthesis is depicted in scheme 5:

(PCT/WO 95/33743). Intermediates of formulas XVI' or XX are reacted with a suitable piperazine derivative to afford intermediates of formula VI. These reactions are performed by conventional methods well known to those skilled in the art. Usually the condensation is carried out in an aprotic (e.g acetonitrile, dimethylformamide, toluene, dioxane, tetrahydrofuran) or protic solvent (e.g. ethanol, n-butanol) or without any solvent, in the presence or absence of a base (e.g. triethylamine, diisopropylethylamine, pyridine, 4-dimethylaminopyridine, potassium carbonate) at a temperature between room temperature and 180° C.

Another method for synthesizing the compounds of the invention comprises alkylating an azaanion of amides of the formula XXI, above, wherein R and Het have the same meanings specified above.

The azaanion may be formed by using a base (e.g. sodium amide, butyl lithium, lithium diisopropylamide, sodium hydride, etc.) and the alkylating agent may be, for example, a compound of formula X—$(CH_2)_n$—$CH(R_3)$—$X_1$, where Scheme 5

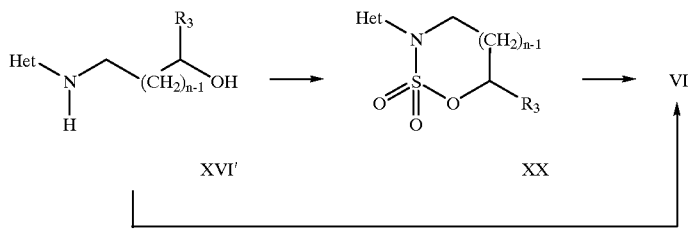

where Het, n and $R_3$ have the same meanings as above and $X_1$ is OH.

Especially when Het is 2-pyridyl, but also in other cases, amino alcohol XVI' obtained as described in Scheme 3, can be converted into a reactive oxathiazolidine-2,2-dioxide XX $X_1$ can be Br, Cl, OH or protected OH (e.g. O-tetrahydropyranyl) obtaining compounds of formula XVIII (X=leaving group), or XVIII' ($X_1$=OH), as described above. As depicted in Scheme 6, compounds XVIII' can conveniently be converted into compounds XVIII through the already described halogenation procedure (preceeded or not by a deprotection step).

Scheme 6

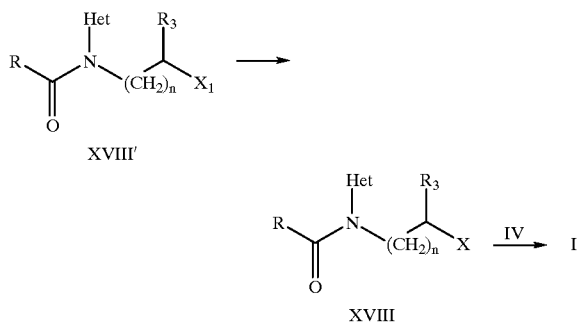

Compounds of formula XVIII' ($X_1$=OH) can also be prepared by acylating compounds with formula XVI by conventional procedures, followed by alkaline hydrolysis of the esters obtained thereby.

A further method to obtain the compounds of the invention comprises alkylating the azaanion of amides XXI with a 1-(ω-X-alkyl)-4-Z-B derivative of formula XVII (X=leaving group e.g. Br, Cl, I, p-toluenesulfonyloxy, methanesulfonyloxy). The azaanion of amides XXI can be formed and alkylated by the use of a base (e.g. butyl lithium, sodium amide, sodium hydride, lithium diisopropyl amide, lithium bis(trimethylsylil)amide or other known to those skilled in the art) in a proper aprotic solvent such as toluene, tetrahydrofuran, dimethoxyethane, dioxane, diglyme or others, at temperatures between −20° C. and the reflux temperature of the solvent.

The compounds of the invention of formula Ia wherein $R_1$ is nitro can be easily converted into compounds of formula I where $R_1$ is amino, acylamino, or alkylsulfonylamino by conventional reaction procedures, such as by reduction of the nitro group via catalytic hydrogenation, transfer hydrogenation or well-known chemical methods to afford amino compounds with formula I, which can be then properly acylated or methansulfonylated by known methods.

The following examples are provided merely to illustrate the invention and its advantages, and are not meant in any way to constitute a limitation on the scope of the invention. The invention is meant to encompass those obvious modifications of the compounds and methods described herein.

EXAMPLE 1

1-[N-cyclohexylcarbonyl-N-(2-pyridyl)-2-aminoethyl]-4-(2-trifluoromethoxyphenyl)piperazine a) N-(2,2-dimethoxyethyl)-N-(2-pyridyl)cyclohexanecarboxamide (Compound 1A)

To a solution comprising 5.97 g 2-(2,2-dimethoxyethylamino)pyridine (prepared as described by I. Kaye, in *J. Am. Chem. Soc.*, 73, 5467 (195 1)) in 40 mL tetrahydrofurane, stirred under a nitrogen atmosphere at 0° C., was added, in a dropwise manner, 13.1 mL butyl lithium (2.5 M, in hexane). This was followed by removal of the cooling bath, and stirring of the obtained mixture for 1 h, at room temperature. There was then added, in a dropwise manner, 4.46 mL cyclohexanecarbonyl chloride. Then, after 5.5 h stirring at room temperature, 2 mL methanol was added. The solution was then evaporated to dryness under a vacuum, yielding a chestnut-colored oil; this product was then purified by flash chromatography (chloroform—ethyl acetate 7:3). The fractions containing the product were evaporated to dryness affording 8.3 g of Compound 1A (yield 78%); this substance was suitable for use in subsequent reactions with no additional purification processing.

$^1$H-NMR 200 MHz (CDCl$_3$, δ): 8.50 (dd, 1H, H6); 7.75 (dt, 1H, H4); 7.30 (d, 1H, H3); 7.20 (dt, 1H, H5); 4.65 (t, 1H, C$\underline{H}$(OCH$_3$)$_2$); 3.90 (d, 2H, C$\underline{H}_2$CH); 3.31 (s, 6H, 2 OCH$_3$); 2.20–2.43 (m, 1H, CHC(O)); 0.80–1.80 (m, 10H, cyclohexyl protons).

b) N-formylmethyl-N-(2-pyridyl)cyclohexanecarboxamide (Compound 1B)

A solution consisting of 0.6 g of Compound 1A, 0.02 g of hydroquinone in 10 mL of 2 N HCl was stirred, under a nitrogen atmosphere, for 0.5 h at a temperature of 80° C. The resultant mixture was then cooled with a water bath and ice, followed by alkalinization with a 5% aqueous sodium carbonate solution (pH=9), and then by extraction with dichloromethane (2×10 mL). The obtained organic phase was dried over anhydrous sodium sulphate and evaporated to dryness. The obtained end-product material (Compound 1B; yield 68%) was suitable for use in subsequent reactions, with no additional purification processing.

$^1$H-NMR 200 MHz (CDCl$_3$, δ): 9.66 (s, 1H, CHO); 8.50 (dd, 1H, H6); 7.79 (dt, 1H, H4); 7.20–7.38 (m, 2H, H3, H5); 4.52 (s, 2H, C$\underline{H}_2$CHO); 2.37–2.55 (m, 1H, CHC(O)); 0.80–1.80 (m 10H, cyclohexyl protons).

c) 1-[N-cyclohexylcarbonyl-N-(2-pyridyl)-2-aminoethyl]-4-(2-trifluoromethoxyphenyl)piperazine A mixture comprising 0.459 g of Compound 1B, 0.445 g of 1-(2-trifluoromethoxyphenyl)piperaine (prepared as described by D. Clarke et al, in European Patent EP 711 757, 1996), 0.634 g sodium triacetoxyborohydride, 0.23 mL of glacial acetic acid and 15 mL of 1,2-dichloroethane was stirred for 4 h, under a nitrogen atmosphere. The resultant solution was then kept overnight at room temperature, followed by the addition of 10 mL of water, and alkalinization with a 20% aqueous Na$_2$CO$_3$ solution. This was followed by separation of phases, with the isolated aqueous phase being extracted with 2×20 mL dichloromethane, and with the collected organic phases being dried over anhydrous sodium sulphate. This was followed by the removal of solvents, via vacuum evaporation to dryness. The obtained product residue was purified by flash chromatography (ethyl acetate—petroleum ether gradient 90:10 to 10:0). This was followed by evaporation of the solvents, affording 0.44 g of the title compound (yield 51%).

$^1$H-NMR 200 MHz (CDCl$_3$, δ): 8.52 (dd, 1H, pyridine H6); 7.74 (ddd, 1H, pyridine H4); 7.16–7.34 (m, 4H, pyridine H3 and H5, 2 aromatics of trifluoromethoxyphenyl); 6.33–7.02 (m, 2H, 2 aromatics of trifluoromethoxyphenyl); 3.97 (t, 2H, C(O)NC$\underline{H}_2$CH$_2$); 2.85–3.05 (m, 4H, piperazine protons); 2.45–2.70 (m, 6H, piperazine protons, C(O)NCH$_2$C$\underline{H}_2$); 2.10–2.32 (m, 1H, CHC(O)); 0.80–1.80 (2m, 10H, cyclohexyl protons).

EXAMPLE 2

1-[N-cyclohexylcarbonyl-N-(2-pyridyl)-2-aminoethyl]-4-[2-(2,2,2-trifluoroethoxy)phenyl] piperazine This compound was prepared as described above, in Example 1, with the exception that, in place of 1-(2-trifluoromethoxyphenyl)piperazine, 1-[2-(2,2,2-trifluoroethoxy)phenyl]piperazine was used (prepared as described by G. Bantle et al, in European Patent EP 748 800, 1996). The obtained residue was purified by flash chromatography (ethyl acetate—petroleum ether gradient 90:10 to 10:0). The evaporation of the solvents afforded the title compound at a yield of 51%.

$^1$H-NMR 200 MHz (CDCl$_3$, δ): 8.46 (dd, 1H, pyridine H6); 7.68 (ddd, 1H, pyridine H4); 7.06–7.28 (m, 2H, pyridine H3 and H5); 6.72–7.02 (m, 4H, aromatics of trifluoroethoxyphenyl); 4.30 (q, 2H, OCH$_2$CF$_3$); 3.91 (t, 2H, C(O)NCH$_2$CH$_2$); 2.80–3.05 (m, 4H, piperazine protons); 2.40–2.55 (m, 6H, piperazine protons, C(O)NCH$_2$CH$_2$); 2.05–2.25 (m, 1H, CHC(O)); 0.70–1.80 (m, 10H, cyclohexyl protons).

EXAMPLE 3

1-[N-cyclohexylcarbonyl-N-(2-pyridyl)-2-aminoethyl]-4-[5-chloro-2-(2,2,2-trifluoroethoxy)phenyl]piperazine This compound was prepared as described above, in Example 1, with the exception that, in place of 1-(2-trifluoromethoxyphenyl)piperazine, 1-[5-chloro-2-(2,2,2-trifluoro-ethoxy) phenyl]piperazine was used (prepared as described by G. Bantle et al, in European Patent EP 748 800, 1996). The obtained residue was purified by flash chromatography (ethyl acetate—petroleum ether gradient 90:10 to 10:0). The evaporation of the solvents afforded the title compound at a yield of 19.5%.

$^1$H-NMR 200 MHz (CDCl$_3$, δ): 8.54 (dd, 1H, pyridine H6); 7.70 (ddd, 1H, pyridine H4); 7.15–7.33 (m, 2H, pyridine H3 and H5); 6.70–6.95 (m, 3H, aromatics of trifluoroethoxyphenyl); 4.32 (q, 2H, OCH$_2$CF$_3$); 3.97 (t, 2H, C(O)NCH$_2$CH$_2$); 2.85–3.10 (m, 4H, piperazine protons); 2.45–2.65 (m, 6H, piperazine protons, C(O)NCH$_2$CH$_2$); 2.10–2.32 (m, 1H, CHC(O)); 0.75–1.85 (2m, 10H, cyclohexyl protons).

EXAMPLE 4

1-[N-cyclohexylcarbonyl-N-(2-pyridyl)-2-aminoethyl]-4-(2-cyanophenyl) piperazine This compound was prepared by the method described above, in Example 1, with the exception that the 1-(2-trifluoromethoxyphenyl)piperazine was replaced here with 1-(2-cyanophenyl)piperazine (prepared as described by Martin et al, in *J. Med. Chem.*, 32, 1052 (1996)). The residue was then purified by flash chromatography (ethyl acetate—petroleum ether gradient 90:10 to 10:0). The evcaporation of the solvents afforded the title compound at a yield of 19.5%.

$^1$H-NMR 200 MHz (CDCl$_3$, δ): 8.55 (dd, 1H, pyridine H6); 7.75 (ddd, 1H, pyridine H4); 7.53–7.75 (dd, 1H, H3 of cyanophenyl); 7.45 (dt, 1H, H5 of cyanophenyl); 7.20–7.30 (m, 2H, pyridine H3 and H5); 6.97 (t, 1H, H4 of cyanophenyl); 6.94 (d, 1H, H6 of cyanophenyl); 3.99 (t, 2H, C(O)NCH$_2$CH$_2$); 3.06–3.19 (m, 4H, piperazine protons); 2.55–2.70 (m, 6H, piperazine protons, C(O)NCH$_2$CH$_2$); 2.35–2.15 (m, 1H, CHC(O)); 0.80–1.80 (2m, 10H, cyclohexyl protons).

EXAMPLE 5

1-[N-cyclohexylcarbonyl-N-(2-pyridyl)-2-aminoethyl]-4-(4-nitro-2-methoxyphenyl)piperazine This compound was prepared by the method described above, in Example 1, except that, instead of 1-(2-trifluoromethoxyphenyl)piperazine, was used 1-(2-methoxy-4-nitrophenyl)piperazine (prepared according to the procedure described by R. Boer et al. in International Patent WO/17831, 1995). The crude product was purified by flash chromatography (ethyl acetate—methanol gradient 98:2 to 95:5). The evaporation of the solvents afforded the title compound at a yield of 60%.

$^1$H-NMR 200 MHz (CDCl$_3$, δ): 8.54 (dd, 1H, pyridine H6); 7.85 (dd, 1H, nitrophenyl H5); 7.75 (ddd, 1H, pyridine H4); 7.68 (d, 1H, nitrophenyl H3); 7.18–7.33 (m,2H, pyridine H3 and H5); 6.85 (d, 1H, nitrophenyl H6); 3.97 (t, 2H, C(O)NCH$_2$CH$_2$); 3.91 (s, 3H, OCH$_3$); 3.05–3.20 (m, 4H, piperazine protons); 2.55–2.70 (m, 6H, piperazine protons, C(O)NCH$_2$CH$_2$); 2.15–2.35 (m, 1H, CHC(O)); 0.80–1.80 (m, 10H, cyclohexyl protons).

EXAMPLE 6

1-[N-cyclohexylcarbonyl-N-(2-pyridyl)-2-aminoethyl]-4-(4-amino-2-methoxyphenyl)piperazine A mixture consisting of 1.70 g of compound of Example 5, 18 mL of tetrahydrofurane, 18 mL of methanol, 50 mg of Nichel-Raney and 1 mL of hydrazine hydrate was stirred for 2 h, at room temperature, followed by the addition of 1 mL of hydrazine hydrate, and stirred for 1 h, at a temperature of 50° C. The catalyst was then filtered out, and the recovered solution was evaporated to dryness, affording the crude product, which was then purified by flash chromatography (ethyl acetate—3 N solution of ammonia, in methanol; 95:5). Subsequent evaporation of the solvents afforded 1.33 g of the title compound (yield 84%).

$^1$H-NMR 200 MHz (CDCl$_3$, δ): 8.52 (dd, 1H, pyridine H6); 7.75 (ddd, 1H, pyridine H4); 7.25–7.35 (m, 2H, pyridine H3 and H5); 6.75 (d, 1H, aminophenyl H6); 624(d 1H, aminophenyl H5); 6.21 (d, 1H, aminophenyl H3); 3.97 (t, 2H, C(O)NCH$_2$CH$_2$); 3.78 (s, 3H, OCH$_3$); 3.00–4.00 (bs, 2H, NH$_2$); 2.78–3.00 (m, 4H, piperazine protons); 2.52–2.70 (m, 6H, piperazine protons, C(O)NCH$_2$CH$_2$); 2.22 (tt, 1H, CHC(O)); 0.80–1.80 (m, 10H, cyclohexyl protons).

EXAMPLE 7

1-[N-cyclohexylcarbonyl-N-(2-pyridyl)-2-aminoethyl]-4-(4-acetylamino-2-methoxyphenyl)piperazine A mixture consisting of 0.35 g of compound of Example 6, 5 mL of chloroform and 0.063 mL of acetyl chloride was stirred for 2.5 h at room temperature, followed by dilution with 50 mL of dichloromethane. The obtained organic phase was then washed with a saturated sodium carbonate solution, and twice with water, followed by drying over anhydrous sodium sulphate and evaporation of the solvents to dryness. The obtained crude product was then purified by flash chromatography (ethyl acetate—3 N solution of ammonia, in methanol; 95:5), and the recovered fraction was evaporated to dryness, affording 0.300 g of the title compound (yield 78%).

$^1$H-NMR 200 MHz (CDCl$_3$, δ): 8.50 (dd, 1H, pyridine H6); 7.75 (ddd, 1H, pyridine H4); 7.12–7.34 (m, 4H, pyridine H3 and H5, methoxyphenyl H6 and NH); 6.75–6.85 (m, 2H, methoxyphenyl H3 and H5); 4.00 (t, 2H, C(O)NCH$_2$CH$_2$); 3.82 (s, 3H, OCH$_3$); 2.80–3.05 (m, 4H, piperazine protons); 2.50–2.71 (m, 6H, piperazine protons and C(O)NCH$_2$CH$_2$); 2.05–2.10 (m, 1H, CHC(O)); 2.14 (s, 3H, CH$_3$CO); 0.80–1.80 (m, 10H, cyclohexyl protons).

EXAMPLE 8

1-[N-cyclohexylcarbonyl-N-(2-pyridyl)-2-aminoethyl]-4-(4-methanesulfonylamino-2-methoxyphenyl)piperazine This compound was prepared by the method described above, in Example 7, but with the substitution of methanesulfonyl chloride for acetyl chloride. The obtained crude residue was purified by flash chromatography (ethyl acetate—3 N ammonia solution, in methanol; 95:5). The solvents were then evaporated off, affording the title compound at a 75% yield.

$^1$H-NMR 200 MHz (CDCl$_3$, δ): 8.50 (d, 1H, pyridine H6); 7.55 (ddd, 1H, pyridine H4); 7.18–7.32 (m, 2H, pyridine H3 and H5); 6.70–6.90 (m, 3H, methoxyphenyl aromatics); 3.95 (t, 2H, C(O)NC$\underline{H}_2$CH$_2$); 3.82 (s, 3H, OCH$_3$); 2.80–3.05 (m, 7H, piperazine protons and CH$_3$S); 2.50–2.72 (m, 6H, piperazine protons and C(O)NCH$_2$C$\underline{H}_2$); 2.05–2.20 (m, 1H, CHC(O)); 0.80–1.80 (m, 10H, cyclohexyl protons).

EXAMPLE 9

1-[N-cyclohexylcarbonyl-N-(2-pyridyl)-2-aminoethyl]-4-(2-carbamoylphenyl)piperazine This compound was prepared by the method described above in Example 1, but using 1-(2-carbamoylphenyl)piperazine (prepared as described in International patent WO14846, 1996) in place of 1-(2-trifluoromethoxyphenyl)piperazine. The crude was purified by flash chromatography (CH$_2$Cl$_2$—MeOH 9.5:0.5). Yield: 9%.

$^1$H-NMR (CDCl$_3$, δ): 9.35–9.55 (br, 1H, CONH($\underline{H}$)), 8.53 (dd, 1H, pyridine H6), 8.13 (dd, 1H, phenyl H6), 7.78 (dd, 1H, pyridine H4), 7.45 (dd, 1H, phenyl H4), 7.10–7.32 (m, 4H, remaining aromatics), 5.60–5.83 (br, 1H, CON$\underline{H}$(H)), 3.97 (t, 2H, CONC$\underline{H}_2$CH$_2$), 2.83–3.00 (m, 4H, piperazine protons), 2.50–2.75 (m, 6H, piperazine protons and CONCH$_2$C$\underline{H}_2$), 2.21 (tt, 1H, CHC(O)), 0.90–1.80 (m, 10H, cyclohexyl protons).

EXAMPLE 10

1-[N-cyclohexylcarbonyl-N-(2-pyridyl)-2-aminoethyl]-4-(2,5-dichlorophenyl)piperazine This compound was prepared as described above, in Example 1, with the exception that, in place of 1-(2-trifluoromethoxyphenyl)piperazine, 1-(2,5-dichlorophenyl)piperazine was used (prepared as described by R. Ratouis et al, in *J. Med. Chem.* 1965, 8, 104–107). The obtained residue was purified by flash chromatography (ethyl acetate—methanol 9:1) affording the title compound (45,6%) as an amorphous ivory solid.

$^1$H-NMR 200 MHz (CDCl$_3$, δ): 8.85 (dd, 1H, pyridine H6); 8.08 (ddd, 1H, pyridine H4); 7.50–7.67 (m, 3H, pyridine H3 and H5, dichlorophenyl H3); 7.27 (s, 1H, dichlorophenyl H6); 7.22 (dd, 1H, dichlorophenyl H4); 4.22–4.50 (t, 2H, C(O)NC$\underline{H}_2$); 3.15–3.38 (m, 4H, piperazine protons); 2.80–3.01 (m, 6H, piperazine protons, C(O)NCH$_2$CH$_2$); 2.45–2.65 (m, 1H, CHC(O)); 1.15–2.15 (m, 10H, cyclohexyl protons).

EXAMPLE 11

1-[N-cyclohexylcarbonyl-N-(2-pyridyl)-2-aminoethyl]-4-(2-methoxy-4-pivaloylaminophenyl)piperazine This compound was prepared as described above, in Example 7, but using pivaloyl chloride in place of acetyl chloride. The obtained residue was purified by flash chromatography (ethyl acetate—2.2 N methanolic ammonia 9.5:0.5) affording the title compound (49%).

$^1$H-NMR 200 MHz (CDCl$_3$, δ): 8.50 (d, 1H, pyridine H6); 7.87 (ddd, 1H, pyridine H4); 7.48 (d, 1H, phenyl H3); 7.18–7.25 (m, 3H, pyridine H3 and H5 and NH); 6.70–6.90 (m. 2H, phenyl H5,6); 3.95–4.15 (m, 2H, C(O)NC$\underline{H}_2$CH$_2$); 3.85 (s, 3H, OCH$_3$); 2.45–3.30 (m,10H, piperazine protons and C(O)NCH$_2$C$\underline{H}_2$); 2.25 (s, 1H, CHC(O)); 0.85–1.80 (m, 19H, cyclohexyl protons and (CH$_3$)$_3$C).

EXAMPLE 12

1-[N-cyclohexylcarbonyl-N-(2-pyridyl)-2-aminoethyl]-4-(4-butanoyl amino-2-methoxyphenyl)piperazine This compound was prepared as described above, in Example 7, but using butanoyl chloride in place of acetyl chloride. The obtained residue was purified by flash chromatography (ethyl acetate—2.2 N methanolic ammonia 9.5:0.5) affording the title compound (53%).

$^1$H-NMR 200 MHz (CDCl$_3$, δ): 8.50 (d, 1H, pyridine H6); 7.87 (ddd, 1H, pyridine H4); 7.40 (d, 1H, phenyl H3); 7.18–7.35 (m, 2H, pyridine H3 and H5); 7.10 (s, 1H, NH); 6.75–6.85 (bs, 2H, phenyl H5,6); 4.00 (s, 2H, C(O)NC$\underline{H}_2$CH$_2$); 3.85 (s, 3H, OCH$_3$); 2.85–3.10 (m, 4H, piperazine protons); 2.55–2.80 (m, 6H, piperazine protons and C(O)NCH$_2$C$\underline{H}_2$); 2.15–2.30 (m, 3H, CHC(O) and NHCOC$\underline{H}_2$); 0.85–1.80 (m, 15H, cyclohexyl protons and CH$_3$CH$_2$).

EXAMPLE 13

1-[N-cyclohexylcarbonyl-N-(2-pyridyl)-2-aminoethyl]-4-(2-bromo-5-methoxybenzyl)piperazine This compound was prepared as described above in Example 1, with the exception that, in place of 1-(2-trifluoromethoxyphenyl)piperazine, 1-(2-bromo-5-methoxybenzyl)piperazine was used (prepared as described in AU9671773). The crude was purified by flash chromatography (EtOAc-MeOH gradient 100:0 to 100:3). Yield: 52% as a yellow thick oil.

$^1$H-NMR 200 MHz (CDCl$_3$, δ): 8.50 (dd, 1H, pyridine H6), 7.60 (ddd, 1H, pyridine H4), 7.39 (d, 1H, bromophenyl ring H3), 7.32–7.15 (m, 2H, pyridine H3 and H5), 7.15–6.95 (m, 1H, bromophenyl ring H6), 6.65 (dd, 1H, bromophenyl ring H4), 4.05–3.88 (m, 2H, CONC$\underline{H}_2$CH$_2$), 3.80 (s, 3H, OCH$_3$), 3.56 (s, 2H, benzylic CH$_2$), 2.80–2.32 (m, 10H, CONCH$_2$C$\underline{H}_2$ and piperazine protons), 2.32–2.10 (m, 1H, CHC(O)), 1.82–0.82 (m, 10H, cyclohexyl protons).

EXAMPLE 14

1-[N-cyclohexylcarbonyl-N-(2-pyridyl)-2-aminoethyl]-4-(2,5-dichlorobenzyl)piperazine a) 1-(2,5-dichlorobenzyl)-4-ethoxycarbonylpiperazine (Compound 14A)

To a mixture comprising 1.94 g 1-ethoxycarbonylpiperazine and 3.45 g anhydrous potassium carbonate, in 20 mL of N,N-dimethylformamide, stirred at room temperature, under a nitrogen atmosphere, there was added 2.01 g of 2,5-dichlorobenzyl chloride. Then after 24 hr stirring at room temperature, this reaction mixture was poured into 200 mL of water, followed by extraction with ethyl acetate (3×100 mL). The obtained organic phase was dried over anhydrous sodium sulphate, followed by evaporation under vacuum. The obtained residue was then purified by flash chromatography (petroleum ether—ethyl acetate 85:15). The solvents were then evaporated off completely to give 2 g of Compound 14A (yield 63%).

$^1$H-NMR 200 MHz (CDCl$_3$, δ): 7.50 (d, 1H, H6); 7.27 (d, 1H, H3); 7.15 (dd, 1H, H4); 4.13 (q, 2H, CH$_3$C$\underline{H}_2$O); 3.58

(s, 2H, benzyl CH$_2$); 3.50 (m, 4H, piperazine protons 2.47 (m, 4H, piperazine protons); 1.26 (t, 3H, C$\underline{H}_3$CH$_2$O).

b) 1-(2,5-dichlorobenzyl)piperazine (Compound 14B)

A solution of 13 g of Compound 14A in 35 mL of 37% HCl was first stirred at reflux for a period of 40 hr, followed by the addition of 30 mL water and 30 mL ethyl acetate, with the pH level adjusted to 11 through addition of a suitable quantity of 35% NaOH. The obtained organic phase was then dried over anhydrous sodium sulphate, followed by evaporation under vacuum. The obtained crude product residue was then purified by flash chromatography (chloroform—methanol 7:3). By this means, 4.46 g of Compound 14B (yield 50%) was obtained.

$^1$H-NMR 200 MHz (CDCl$_3$, δ): 7.50 (d, 1H, H6); 7.26 (d, 1H, H3); 7.14 (dd, 1H, H4); 3.55 (s, 2H, benzyl CH$_2$); 3.00–2.85 (m, 4H, piperazine protons); 2.55–2.48 (m, 4H, piperazine protons); 1.76 (s, 1H, NH).

c) 1-[N-cyclohexylcarbonyl-N-(2-pyridyl)-2-aminoethyl]-4-(2,5-dichlorobenzyl)pipe-razine methanesulfonate hemihydrate To a mixture comprising 0.164 g of Compound 1B of Example 1, 0.210 g of Compound 14B, and 4 mL methanol, continuously stirred under nitrogen, at room temperature, there was added 0.049 g of sodium cyanoborohydride. The resulting mixture was then stirred for 13 hr, at room temperature, followed by dilution with 10 mL water, and subsequent extraction with ethyl acetate (3×10 mL). The collected organic phases were then dried over anhydrous sodium sulphate, followed by vacuum evaporation, and subsequent purification of the obtained product residue by flash chromatography (chloroform—methanol 95:5). The solvents were then evaporated off, from the recovered fractions, yielding a residual substance which was then solubilized into 2 mL ethyl acetate. To this solution was then added 0.08 mL methanesulphonic acid (2 M solution of CH$_3$SO$_3$H, in ethanol) followed by diethyl ether, until the complete precipitation of the product. 0.071 g of this end-product precipitate was recovered here (yield 19%), through the use of vacuum filtration procedures.

$^1$H-NMR 200 MHz (CDCl$_3$, δ): 8.51 (dd, 1H, pyridine H6); 7.83 (ddd, 1H, pyridine H4); 7.12–7.50 (m, 6H, pyridine H3 and H5, phenyl protons and NH$^+$); 4.10–4.25 (m, 2H, C(O)NC$\underline{H}_2$CH$_2$); 3.50–3.85 (m, 4H, piperazine protons); 3.15–3.40 (m, 2H, C(O)CH$_2$C$\underline{H}_2$); 2.75–3.15 (m, 6H, piperazine protons, benzyl CH$_2$); 2.74 (s, 3H, CH$_3$S); 2.33–2.18 (m, 1H, cyclohexyl H1); 0.80–1.80 (2m, 11H, cyclohexyl protons, 0.5 H$_2$O).

EXAMPLE 15

1-[N-cyclohexylcarbonyl-N-(2-pyridyl)-2-aminoethyl]-4-benzylpiperazine

A mixture of 0.3 g of Compound 1B, 0.2 mL of 1-benzylpiperazine, 0.14 mL of acetic acid, 0.38 g of sodium triacetoxyborohydride and 7 mL of methylene chloride was stirred at room temperature for 24 h. Afterwards, it was diluted with water, alkalinized with 5% aq. sodium hydrogencarbonate. The organic layer was separated, dried on sodium sulphate and evaporated to dryness in vacuo affording a crude, which was purified by flash chromatography (methylene chloride—methanol 9.5:0.5) affording 0.03 g (3.6% overall from Compound 1A) of the title product.

$^1$H-NMR 200 MHz (CDCl$_3$, δ): 8.50 (dd, 1H, pyridine H6); 7.75 (ddd, 1H, pyridine H4); 7.10–7.40 (m, 7H, pyridine H3 and H5, phenyl protons); 4.00 (t, 2H, C(O)NC$\underline{H}_2$); 3.60 (s, 2H, PhCH$_2$); 2.30–2.90 (m, 10H, piperazine protons, C(O)NCH$_2$C$\underline{H}_2$); 2.10–2.25 (m, 1H, CHC(O)); 0.80–1.80 (m, 10H, cyclohexyl protons).

EXAMPLE 16

1-[N-cyclohexylcarbonyl-N-(2-pyridyl)-2-aminoethyl]-4-(2-phenylethyl)piperazine

This product was prepared as described in Example 2, with the exception that 1-benzylpiperazine was replaced by 1-(2-phenylethyl)piperazine (prepared as described in Beil. EIII/IV, 62). The crude was purified by flash chromatography (chloroform—methanol 9.7:0.3) affording of the title product (61%).

$^1$H-NMR 200 MHz (CDCl$_3$, δ): 8.51 (dd, 1H, pyridine H6); 7.75 (ddd, 1H, pyridine H4); 7.10–7.20 (m, 7H, pyridine H3 and H5, phenyl protons); 3.96 (t, 2H, C(O)NC$\underline{H}_2$); 2.45–2.90 (m, 14H, PhC$\underline{H}_2$CH$_2$, CH$_2$C$\underline{H}_2$N and piperazine CH$_2$s); 2.20 (tt, 1H, CHC(O)); 0.85–1.80 (m, 10H, cyclohexyl protons).

EXAMPLE 17

1-[N-cyclohexylcarbonyl-N-(2-pyridyl)-2-aminoethyl]-4-benzoyl piperazine

This product was prepared as described in Example 2, with the exception that 1-benzylpiperazine was replaced by 1-benzoylpiperazine (prepared as described by K.-R. Jacobi Chem. Ber. 1933, 113–116). The crude product was purified by flash chromatography (chloroform—methanol 9.75:0.25) affording the title product (54%).

$^1$H-NMR 200 MHz (CDCl$_3$, δ): 8.51 (dd, 1H, pyridine H6); 7.75 (ddd, 1H, pyridine H4); 7.15–7.45 (m, 7H, pyridine H3 and H5, phenyl protons); 3.95 (t, 2H, CONC$\underline{H}_2$CH$_2$N) 3.45–3.80 (m, 2H, eq. H3 and H5 piperazine protons); 3.15–3.45 (m, 2H, ax. H3 and H5 piperazine protons); 2.30–2.65 (m, 6H, CH$_2$C$\underline{H}_2$N and remaining piperazine CH$_2$s); 2.18 (tt, 1H, CHCO); 0.85–1.80 (m, 10H, cyclohexyl protons).

EXAMPLE 18

1-[N-cyclohexylcarbonyl-n-(2-pyridyl)-2-aminoethyl]-4-benzoylmethylpiperazine hydrochloride This compound was prepared by the method described above, in Example 1, except that, instead of 1-(2-trifluoromethoxyphenyl)piperazine, was used 1-benzoylmethylpiperazine (prepared according to the procedure described in Beil. 23, V/2, 200). The crude was purified by flash chromatography (ethyl acetate—2 N methanolic ammonia gradient 97:3 to 95:5). The residue obtained by evaporation of the collected fractions was dissolved in ethyl acetate, excess of 5 N isopropanolic HCl was added and the precipitate was collected by filtration to give the title compound at a yield of 18%. M. p. 225–228° C. dec.

$^1$H-NMR 200 Mhz (DMSO-d$_6$, δ): 8.55 (dd, 1H, pyridine H6); 7.90–8.00 (m, 3H, pyridine H4, phenyl H2 and H6); 7.70 (dd, 1H, pyridine H3); 7.50–7.65 (m, 3H, phenyl H3, H4 and H5); 7.35–7.50 (ddd, 1H, phenyl H5); 5.30–6.80 (bs, 1H, NH$^+$); 5.05 (S, 2h, CH$_2$CO); 4.05 (T, 2h, CH$_2$NCO); 3.45–3.65 (M, 8h, piperazine protons); 3.30 (t, 2H, C$\underline{H}_2$, CH$_2$NCO); 2.20 (q, 1H, CHC(O)); 0.80.1.70 (m, 10H, cyclohexyl protons).

EXAMPLE 19

1-[N-cyclohexylcarbonyl-N-(2-pyridyl)-2-aminoethyl]-4-(2-hydroxy-2-phenylethyl)piperazine To a solution of 0.18 g of compound of Example 18 in 4.2 mL of methanol was added at 10° C. 0.158 g of sodium borohydride. After 3 h stirring at r.t. and overnight resting, the solvent was removed and the residue was treated with $H_2O$ and extracted with ethyl acetate. The crude product obtained after solvent evaporation, was purified by flash chromatography (ethyl acetate—2N methanolic ammonia 97.5:2.5 to give 0.112 g (61%) of the title compound. mp 140–142° C.

$^1$H-NMR 200 MHz (CDCl$_3$, δ): 8.55 (dd, 1H, pyridyne H6); 7.75 (ddd, 1H, pyridyne H4); 7.20–7.40 (m, 7H, pyridyune H3 and H5, phenyl CHs); 4.65–4.80 (dd, 1H C$\underline{H}$OH); 3.90–4.05 (m, 3H, OH, CH$_2$NCO); 2.30–2.80 (m, 12H, piperazine protons, C$\underline{H}_2$CHOH, C$\underline{H}_2$CH$_2$NCO); 2.15–2.30 (q, 1H CHC(O)); 0.90–1.80 (m, 10H cyclohexyl protons).

EXAMPLE 20

1-[N-cyclohexylcarbonyl-N-(2-pyridyl)-2-aminoethyl]-4-(2-methoxy-4-trifluoroacetylaminophenyl)piperazine To a solution of 0.56 g of the compound of Example 6 in 10 mL of chloroform was added at room temperature 0.30 mL of trifluoroacetic anhydride. The resulting solution was stirred at room temperature for 4 h and then diluted with 50 mL of chloroform, washed with 0.5 N NaOH and twice with water, dried on sodium sulphate and evaporated to dryness in vacuo. The crude was purified by flash chromatography (ethyl acetate—2N ammonia in methanol 98:2), to afford 0.39 g (70%) of the title product. M.p. 144–148 ° C.

$^1$H-NMR, 200 MHz (CDCl$_3$, δ): 8.50–8.54 (m, 1H, pyridine H6); 7.80–8.42 (br, 1H NH); 7.78 (ddd, 1H pyridine H4); 7.15–7.50 (m, 3H, pyridine H3 and H5, phenyl H3); 6.98 (dd, 1H phenyl H5); 6.87 (d, 1H, phenyl H6); 3.95–4.44 (m, 2H, C(O)NC$\underline{H}_2$CH2); 3.83 (s, 3H OCH$_3$); 2.38–3.70 (m, 10H, piperazine protons and C(O)NCH$_2$C$\underline{H}$2); 2.13–2.35 (m, 1H, CHC(O)); 0.80–1.85 (m, 10H, cyclohexyl protons).

EXAMPLE 21

1-[N-cyclohexylcarbonyl-N-(2-pyridyl)-2-aminoethyl]-4-(4-ethylamino-2-methoxyphenyl) piperazine
a) 1-[N-cyclohexylcarbonyl-N-(2-pyridyl)-2-aminoethyl]-4-[4-(N-ethyl-N-trifluoromethylcarbonylamino)-2-methoxyphenyl]piperazine (Compound 23A)

To a solution of 0.35 g of the compound of Example 22 in 5 mL of anhydrous N,Ndimethylformamide was added at room temperature 36 mg of 60% sodium hydride (oil dispersion) and the resulting mixture was stirred at room temperature for 1 h. Afterwards, 0.07 mL of ethyl bromide was added, the reaction flask was sealed and the mixture was stirred at 60° C. for 2.5 h, cooled to room temperature, poured into 100 mL of water and extracted with ethyl acetate (2×40 mL). The combined extracts were washed with water, dried on sodium sulphate and evaporated to dryness in vacuo. The crude was purified by flash chromatography (ethyl acetate—2N ammonia in methanol 98:2), affording 0.25 g (65%) of compound 23A.

$^1$H-NMR 200 MHz (CDCl$_3$, δ): 8.48–8.57 (m, 1H, pyridine H6); 7.79 (ddd, 1H, pyridine H4); 7.21–7.41 (m, 2H, pyridine H3 and H5); 6.80–6.94 (m, 2H, phenyl H5 and H6); 6.63 (bs, 1H, phenyl H3); 3.93–4.22 (m, 2H C(O)NC$\underline{H}_2$CH$_3$); 3.85 (s, 3H, OCH$_3$); 3.65–3.88(m, 2H, CH$_3$C$\underline{H}_2$); 2.38–3.40 (m, 10H piperazine protons and C(O)NCH$_2$C$\underline{H}_2$); 2.13–2.33 (m, 1H, CHC(O)); 0.78–1.83 (m, 13H, cyclohexyl protons and C$\underline{H}_3$CH$_2$).

b) 1-[N-cyclohexylcarbonyl-N-(2-pyridyl)-2-aminoethyl]-4-(4-ethylamino-2-methoxyphenyl]piperazine To a solution of 0.21 g of compound 23A in 5 mL of ethanol was added 0.076 g of sodium borohydride. The reaction mixture was stirred at room temperature for 3 h, diluted with water and extracted with chloroform (3×50 mL). The combined organic layers were washed with water, dried on sodium sulphate and evaporated to dryness in vacuo. The crude was purified by flash chromatography (ethyl acetate—2N ammonia in methanol 97:3), affording 0.11 g (64%) of the title compound. M.p. 107–110° C.

$^1$H-NMR 200 MHz (CDCl$_3$, δ): 8.48–8.57 (m, 1H, pyridine H6); 7.77 (ddd, 1H pyridine H4); 7.14–7.40 (m, 2H, pyridine H3 and H5); 6.72–6.89 (m, 1H, phenyl H5(H6)); 6.09–6.12 (m, 2H, phenyl H3 and H6(H5)); 3.92–4.25 (m, 2H, C(O)NC$\underline{H}_2$CH$_2$); 3.80 (s, 3H, OCH$_3$); 2.39–3.50 (m, 13H, piperazine protons, C(O)NCH$_2$C$\underline{H}_2$, C$\underline{H}_2$CH$_3$ and NH); 2.13–2.37 (m, 1H, CHC(O)); 0.83–1.85 (m, 13H, cyclohexyl protons and C$\underline{H}_3$CH$_2$).

EXAMPLE 22

1-[N-cyclohexylcarbonyl-N-(2-pyridyl)-2-aminoethyl]-4-(4-diethylamino-2-methoxyphenyl) piperazine To a solution of 0.17 g of the compound of Example 6 and 0.20 mL of acetaldehyde in 5 mL of methanol was added 0.14 g of 85% sodium cyanoborohydride and the resulting mixture was stirred at room temperature for 8 h. After overnight standing, the mixture was poured into 50 mL water, alkalinized with 1N sodium hydroxide and extracted twice with ethyl acetate. The combined organic layers were dried on sodium sulphate and evaporated to dryness in vacuo. The crude was purified by flash chromatography (ethyl acetate—3N ammonia in methanol 99:1) to afford 0.102 g (50%) of the title product.

$^1$H-NMR 200 MHz (CDCl$_3$, δ): 8.45–8.55 (m, 1H, pyridine H6); 7.78 (ddd, 1H pyridine H4); 7.20–7.42 (m, 2H, pyridine H3 and H5); 6.72–6.89 (m, 1H, phenyl H6(H5)); 6.18–6.35 (m, 2H, phenyl H3 and H5(H6)); 3.95–4.25 (m, 2H, C(O)NC$\underline{H}_2$CH$_2$); 3.82 (s, 3H OCH$_3$); 2.42–3.50 (m, 14H, piperazine protons and C(O)NCH$_2$C$\underline{H}_2$ and (CH$_3$C$\underline{H}_2$)$_2$N); 2.18–2.35 (m, 1H, CHC(O)); 0.83–1.85 (m, 16H cyclohexyl protons and (C$\underline{H}_3$CH$_2$)$_2$N).

EXAMPLE 23

1-[N-cyclohexylcarbonyl-N-(2-pyridyl)-2-aminoethyl]-4-(2-methoxy-4-phenylacetylaminophenyl) piperazine This compound was prepared by the method described above, in Example 7, but with the substitution of phenylacetyl chloride for acetyl chloride. The obtained crude residue was purified by flash chromatography (ethyl acetate—3 N ammonia in methanol 97: 3). The solvents were then evaporated off, affording the title compound at a 67% yield.

$^1$H-NMR 200 MHz (CDCl$_3$ δ): 8.48–8.56 (m, 1H, pyridine H6); 7.75 (ddd, 1H, pyridine H4); 7.12–7.47 (m, 8H, pyridine H3 and H5, benzyl ring CHs and methoxyphenyl H3); 7.05 (bs, 1H, NH); 6.78 (d, 1H methoxyphenyl H6); 6.66 (dd, 1H, methoxyphenyl H5); 4.02 (t, 2H, C(O)NC$\underline{H}_2$CH$_2$); 3.81 (s, 3H, OCH$_3$); 3.72 (s, 1H CH$_2$CO); 2.82–3.10 (m, 4H, piperazine protons); 2.30–2.48 (m, 6H, piperazine protons and C(O)NCH$_2$C$\underline{H}_2$); 2.12–2.35 (m, 1H, CHC(O)); 0.85–1.85 (m, 10H, cyclohexyl protons).

EXAMPLE 24

1-[N-cyclohexylcarbonyl-N-(2-pyridyl)-2-aminoethyl]-4-(4-formylamino-2-methoxyphenyl) piperazine A solution of 0.140 g of the compound of Example 6 and 0.4 mL of formic acid in 8 mL of ethyl acetate was stirred at room temperature for 8 h. Afterwards, the reaction mixture was diluted with 40 mL of ethyl acetate, washed with 1 N sodium hydroxide and water, dried on sodium sulphate and evaporated to dryness in vacuo. The crude was purified by flash chromatography (ethyl acetate—3N ammonia in methanol 95:5) to afford 0. 130 g (89%) of the title product.

$^1$H-NMR 200 MHz (DMSO-d6, δ):10.02 (s, 0.7H CHO); 9.91 (d, 0.3H, CHO); 8.65 (d, 0.3H, NH); 8.45–8.55 (m, 1H, pyridine H6); 8.20 (bs, 0.7H, NH); 7.90 (dd, 1H pyridine H4); 7.45 (d, 1H pyridine H3); 7.32 (ddd, 1H, pyridine H5); 7.25 (s, 0.7 H, phenyl H3); 7.04 (dd, 0.7 H, phenyl H5); 6.57–6.32 (m, 1.6 H, phenyl H6, 0.3 H5 and 0.3 H3); 3.82 (t, 2H C(O)NCH$_2$CH$_2$); 3.73 (s, 0.9H, OCH$_3$); 3.70 (s, 2. 1H OCH$_3$); 2.61–2.90 (m, 4H, piperazine protons); 2.32–2.60 (m, 6H, piperazine protons and C(O)NCH$_2$CH$_2$); 2.10–2.30 (m, 1H, CHC(O)); 0.80–1.80 (m, 10H, cyclohexyl protons).

EXAMPLE 25

1-[N-cyclohexylcarbonyl-N-(2-pyridyl)-2-aminoethyl]-4-[4-nitro-2-(2,2,2-trifluoroethoxy) phenyl)piperazine a) 1-Acetyl-4-[2-(2,2,2-trifluoroethoxy)phenyl]piperazine (Compound 27A)

This compound was prepared by the method described above, in Example 8, except that, instead of the compound of Example 7, 1-[2-(2,2,2-trifluoroethoxy)phenyl]piperazine was used. Flash chromatography afforded compound 27A at a 67% yield.

$^1$H-NMR 200 MHz (CDCl$_3$,δ): 6.82–7.10 (m, 4H, aromatics of trifluoroethoxyphenyl); 4.40 (q, 2H, OCH$_2$CF$_3$); 3.70–3.87 (m, 2H, piperazine protons); 3.52–3.70 (m, 2H, piperazine protons); 2.96–3.13 (m, 4H, piperazine protons); 2.11 (s, 3H, CH$_3$).

b) 1-Acetyl-4-[4-nitro-2-(2,2,2-trifluoroethoxy)phenyl]piperazine (Compound 27B)

To a solution of 1.75 g of the Compound 27A in 30 mL of acetic acid was added 1 mL of 8.7 N nitric acid and the reaction mixture was stirred at room temperature for 1 h and for 2 h at 50° C. Afterwards, the mixture was cooled to room temperature, poured into iced water, alkalinized with 37% sodium hydroxide and extracted with dichloromethane. The extract was dried over sodium sulphate, evaporated to dryness in vacuo and purified by flash chromatography (ethyl acetate—methanol 97:3). Evaporation of the solvents afforded 0.85 g of compound 27B (42%).

$^1$H-NMR 200 MHz (CDCl$_3$, δ): 7.98 (dd, 1H, phenyl H5); 7.70 (d, 1K phenyl H3); 6.94 (d, 1H, phenyl H6); 4.48 (q, 2H, OCH$_2$CF$_3$); 3.48–4.92 (m, 4H, piperazine protons); 3.10–3.32 (m, 4H, piperazine protons); 2.12 (s, 3H CH$_3$).

c) 4-[4-nitro-2-(2,2,2-tiifluoroethoxy)phenyl]piperazine (Compound 27C)

A solution of 0.3 g of the compound 27B in 5 mL of 37% HCl was stirred at reflux for 1.5 h. Afterwards, the mixture was cooled to room temperature, poured into iced water, alkalinized with 37% sodium hydroxide and extracted with dichloromethane. The extract was dried over sodium sulphate and evaporated to dryness in vacuo to afford 0.255 g of compound 27C (97%).

$^1$H-NMR 200 MHz (CDCl$_3$, δ): 7.98 (dd, 1H, phenyl H5); 7.70 (d, 1H, phenyl H3); 6.95 (d, 1H, phenyl H6); 4.48 (q, 2H, OCH$_2$CF$_3$); 3.18–3.40 (m, 4H, piperazine protons); 2.95–3.18 (m, 4H, piperazine protons); 1.70 (bs, 1H, NH).

d) 1-[N-cyclohexylcarbonyl-N-(2-pyridyl)-2-aminoethyl]-4-[4-nitro-2-(2,2,2-trifluoroethoxy)phenyl)piperazine This compound was prepared by the method described above, in Example 1, except that, instead of 1-(2-trifluoromethoxyphenyl)piperazine, compound 27C was used. The crude was purified by flash chromatography (ethyl acetate—petroleum ether 95:5). Evaporation of the solvents afforded the title compound at a yield of 47%.

$^1$H-NMR 200 MHz (CDCl$_3$, δ): 8.54 (dd, 1H, pyridine H6); 7.98 (dd, 1H nitrophenyl H5); 7.78 (ddd, 1H, pyridine H4); 7.69 (d, 1H, nitrophenyl H3); 7.20–7.35 (m, 2H, pyridine H3 and H5); 6.88 (d, 1H, nitrophenyl H6); 4.42 (q, 2H, OCH$_2$CF$_3$); 4.04 (t, 2H, C(O)NCH$_2$CH$_2$); 3.12–3.38 (m, 4H, piperazine protons); 2.57–2.90 (m, 6H, piperazine protons and C(O)NCH$_2$CH$_2$); 2.10–2.32 (m, 1H, CHC(O)); 0.80–1.80 (m, 10H, cyclohexyl protons).

EXAMPLE 26

1-[N-cyclohexylcarbonyl-N-(2-pyridyl)-2-aminoethyl]-4-[4-amino-2-(2,2,2-trifluoroethoxy) phenyl) piperazine This compound was prepared by the method described above, in Example 6, except that, instead of the compound of Example 5, was used the compound of Example 27. The crude product was purified by flash chromatography (ethyl acetate—3 N ammonia in methanol 98:2). Evaporation of the solvents afforded the title compound at a yield of 61%.

$^1$H-NMR 200 MHz (CDCl$_3$, δ): 8.52 (dd, 1H pyridine H6); 7.75 (ddd, 1H pyridine H4); 7.18–7.32 (m, 2H, pyridine H3 and H5); 6.75 (d, 1H, phenyl H6); 6.38 (dd, 1H, phenyl H5); 6.28 (d, 1H, phenyl H3); 4.35 (q, 2H, OCH$_2$CF3); 4.00 (t, 2H, C(O)NCH$_2$CH$_2$); 3.55 (bs, 2H, NH$_2$); 2.78–3.18 (m, 4H, piperazine protons); 2.48–2.78 (m, 6H, piperazine protons, C(O)NCH$_2$CH$_2$); 2.10–2.35 (m, 1H CHC(O)); 0.80–1.82 (m 10H, cyclohexyl protons).

EXAMPLE 27

1-[N-cyclohexylcarbonyl-N-(2-pyridyl)-2-aminoethyl]-4-(2,5-dichlorobenzyloxy)piperazine:

a) 1-Acetyl-4-(2,5-dichlorobenzyl)piperazine (Compound 29A)

This compound was prepared by the method described above, in Example 8, except that, instead of the compound of Example 7, compound 14B was used. Flash chromatography afforded compound 29A at a 67% yield.

b) 1-Acetyl-4-(2,5-dichlorobenzyl)piperazine 4-oxide (Compound 29B)

To a solution of 0.55 g of compound 29A in 10 mL of formic acid was added at 0° C. 1.5 mL of 30% aqueous hydrogen peroxide and the reaction mixture was stirred at room temperature for 16 h. An additional amount of 1 mL of 30% aq. hydrogen peroxide was added and stirring continued for 16 h. Powdered sodium carbonate was added portionwise to obtain pH=7, then, the mixture was extracted with chloroform, filtered, dried over sodium sulphate and evaporated to dryness in vacuo to afford 0.45 g (77.6%) of compound 29B.

$^1$H-NMR 200 MHz (CDCl3, δ): 8.00 (bs, 1H, phenyl CH); 7.38 (bs, 2H, phenyl CHs); 4.60 (bs, 2H, CH$_2$Ph); 4.03–4.25 (m, 1H, piperazine proton); 3.11–3.76 (m, 7H, piperazine protons); 2.10 (s, 3H, CH$_3$CO).

c) 1-Acetyl-4-(2,5-dichlorobenzyloxy)piperazine (Compound 29C)

A solution of 0.32 g of compound 29B in 10 mL of dioxane was refluxed for 6 h. After evaporation to dryness of the solvent, the crude was purified by flash chromatography (ethyl acetate—3N ammonia in methanol 97:3) to afford 0.24 g (75%) of compound 29C.

$^1$H-NMR 200 MHz (DMSO-d6, $\delta$): 7.28–7.55 (m, 3H, phenyl CHs); 4.76 (bs, 2H, CH$_2$Ph); 3.95–4.22; 3.62–3.85; 3.38–3.48; 3.00–3.28; 2.65–2.90; 2.25–2.60 (6m, 8H, protons); 2.10 (s, 3H CH$_3$CO).

d) 1-(2,5-dichlorobenzyloxy)piperazine (Compound 29D)

This compound was prepared by the method described above for compound 27C, replacing compound 27B with compound 29C. Evaporation of the extraction solvent afforded compound 29D at a 90% yield.

$^1$H-NMR 200 MHz (CDCl$_3$, $\delta$): 7.48 (d, 1H phenyl H6); 7.27 (d, 1H, phenyl H3); 7.15 (dd, 1H phenyl H4); 4.78 (s, 2H CH$_2$Ph); 3.10–3.40 (m, 2H, piperazine protons); ); 2.70–3.10 (m, 4H, piperazine protons); 2.40–2.70 (m, 2H, piperazine protons); 2.22 (s, 1H, NH).

e) 1-[N-cyclohexylcarbonyl-N-(2-pyridyl)-2-aminoethyl]-4-(2,5-dichlorobenzyloxy)piperazine This compound was prepared by the method described above, in Example 1, except that, instead of 1-(2-trifluoromethoxyphenyl)piperazine, Compound 29D was used. The crude was purified by flash chromatography (ethyl acetate—methanol 97:3). Evaporation of the solvents afforded the title compound at a yield of 44%.

$^1$H-NMR 200 MHz (CDCl$_3$, $\delta$): 8.48–8.55 (dd,. 1H, pyridine H6); 7.75 (ddd, 1H, pyridine H4); 7.40 (d, 1H phenyl H6); 7.10–7.30 (m, 4H, pyridine H3, H5 and phenyl H3,4); 4.75 (s, 2H CH$_2$Ph); 3.96 (t, 2H C(O)NC$\underline{H}_2$CH$_2$); 3.00–3.30; 2.45–2.92; 2.10–2.40 (3m, 11H, piperazine protons, C(O)NCH$_2$C$\underline{H}_2$ and CHC(O)); 0.85–1.95 (m, 10H, cyclohexyl protons).

EXAMPLE 28

Effects on Volume-Induced Rhythmic Bladder Voiding Contractions in Anaesthetized Rats A. Methods Female Sprague Dawley rats weighing 225–275 g (Crl: CDo BR, Charles River Italia) were used. The animals were housed with free access to food and water and were maintained on a forced 12 h alternating light-dark cycle at 22–24° C. for at least one week, except during the experiment. The activity on the rhythmic bladder voiding contractions was evaluated according to the method of Dray (J. Pharmacol. Methods, 13:157, 1985), with some modifications as in Guarneri (Pharmacol. Res., 27:173, 1993). Briefly, rats were anesthetized by subcutaneous injection of 1.25 g/kg (5 ml/kg) urethane, after which the urinary bladder was catheterized via the urethra using PE 50 polyethylene tubing filled with physiological saline. The catheter was tied in place with a ligature around the external urethral orifice and was connected with conventional pressure transducers (Statham P23 ID/P23 XL). The intravesical pressure was displayed continuously on a chart recorder (Battaglia Rangoni KV 135 with DCl/TI amplifier). The bladder was then filled via the recording catheter by incremental volumes of warm (37° C.) saline until reflex bladder voiding contractions occurred (usually 0.8–1.5 ml). For intravenous (i.v.) injection of bioactive compounds, PE 50 polyethylene tubing filled with physiological saline was inserted into the jugular vein.

From the cystometrogram, the number of contractions recorded 15 min before (basal values) and after treatment, as well as the mean amplitude of these contractions (mean height of the peaks in mmHg) was evaluated.

Since most compounds produced an effect that was relatively rapid in onset and led to a complete cessation of bladder contractions, bioactivity was conveniently estimated by measuring the duration of bladder quiescence (i.e., the duration of time during which no contractions occurred). After cessation of the effect of drug injection, the height of the peaks was compared with that previously recorded after the intravenous administration of vehicle alone. The potency of the tested compounds (ED$_{50}$ value: the extrapolated doses inducing 30% reduction of amplitude of the contractions in 50% of treated rats) was evaluated on a quantal basis by the method of Bliss (Bliss C. I., Quart. J. Pharm. Pharmacol. 11, 192–216, 1938).

B. Results

The rapid distension of the urinary bladder in urethane-anesthetized rats produced a series of rhythmic bladder voiding contractions whose characteristics have been described (Maggi et al., Brain Res., 380:83, 1986; Maggi, et al., J. Pharmacol. Exp. Ther., 230:500, 1984). The frequency of these contractions is related to the sensory afferent arm of reflex micturition and to the integrity of the micturition center, while their amplitude is a property of the efferent arm of the reflex. In this model system, compounds that act mainly on the CNS (such as morphine) cause a block in voiding contraction, whereas drugs that act at the level of the detrusor muscle, such as oxybutynin, lower the amplitude of the bladder contractions.

The results obtained with the tested compounds are shown in Table 1. All the compounds of the present invention produced better results than could be achieved with Compound A with regard to the disappearance time of bladder contractions. They also resulted in a longer time of suppression of contractions than flavoxate.

Oxybutynin only decreased the amplitude of the contractions in a dose-related manner, with an ED$_{50}$ value (the extrapolated dose inducing a 30% reduction of amplitude of the contractions in 50% of treated rats) of 240 mg/kg. That is, oxybutynin does not cause cessation of bladder contractions. This amplitude-reduction effect characteristic of oxybutynin, which can potentially cause lower bladder contractility and the undesirable retention of residual urine in the bladder after micturition, is not characteristic of the compounds of the invention.

TABLE 1

Effects on rhythmic bladder voiding contractions after intravenous administration. Data represent mean values ± S.E. of the duration of bladder quiescence (disappearance time of contractions in min after i.v. administration of compound).

| Compound | Dose ($\mu$g/kg) | Bladder Quiescence |
| --- | --- | --- |
| Compound A | 3 | 2.99 ± 0.63 |
|  | 10 | 8.31 ± 1.28 |
|  | 30 | 9.52 ± 0.82 |
|  | 100 | 11.25 ± 1.09 |
|  | 1000 | 6.30 ± 1.42 |
|  | 3000 | 9.25 ± 2.77 |
| Ex. 1 | 100 | 5.85 ± 1.87 |
|  | 1000 | 16.25 ± 1.38 |
|  | 3000 | 18.40 ± 4.12 |
| Ex. 2 | 30 | 3.00 ± 0.91 |
|  | 100 | 8.70 ± 2.88 |
|  | 1000 | 27.28 ± 8.70 |
| Ex. 3 | 10 | 3.15 ± 1.74 |
|  | 100 | 6.15 ± 1.19 |
|  | 1000 | 10.13 ± 0.59 |
|  | 3000 | 14.42 ± 2.36 |

TABLE 1-continued

Effects on rhythmic bladder voiding contractions after intravenous administration. Data represent mean values ± S.E. of the duration of bladder quiescence (disappearance time of contractions in min after i.v. administration of compound).

| Compound | Dose (µg/kg) | Bladder Quiescence |
|---|---|---|
| Ex. 6 | 10 | 6.75 ± 1.66 |
|  | 100 | 9.82 ± 1.18 |
|  | 1000 | 15.00 ± 3.11 |
| Ex. 7 | 100 | 7.97 ± 1.78 |
|  | 300 | 8.65 ± 1.81 |
|  | 1000 | 20.63 ± 3.31 |
| Ex. 8 | 100 | 2.03 ± 0.44 |
|  | 1000 | 7.20 ± 1.07 |
|  | 3000 | 14.20 ± 2.57 |
| Ex. 14 | 30 | 2.80 ± 1.31 |
|  | 100 | 10.12 ± 1.98 |
|  | 300 | 21.52 ± 4.66 |
| Flavoxate | 1000 | 3.04 ± 0.96 |
|  | 3000 | 5.30 ± 1.00 |
|  | 10000 | 8.25 ± 1.90 |
|  | 100 | 0.92 ± 0.15 |
|  | 300 | 2.87 ± 1.12 |
|  | 1000 | 2.80 ± 0.60 |
|  | 3000 | 6.27 ± 2.90 |

EXAMPLE 29

Radioreceptor Binding to recombinant 5-HT$_{1A}$ receptors

A. Methods

Genomic clone G-21 coding for the human 5-HT$_{1A}$-serotoninergic receptor is stably transfected in a human cell line (HeLa). HeLa cells were grown as monolayers in Dulbecco's modified Eagle's medium (DMEM), supplemented with 10% fetal calf serum and gentamicin (100 mg/ml), 5% $CO_2$ at 37° C. Cells were detached from the growth flash at 95% confluence by a cell scraper and were lysed in ice-cold 5 mM Tris and 5 mM EDTA buffer (pH 7.4). Homogenates were centrifuged at 40000×g×20 min and pellets were resuspended in a small volume of ice-cold 5 mM Tris 5 and 5 mM EDTA buffer (pH 7.4) and immediately frozen and stored at −70° C. until use. On the day of experiment, cell membranes were resuspended in binding buffer: 50 mM Tris HCl (pH 7.4), 2.5 mM $MgCl_2$, 10 mM pargiline (Fargin et al., Nature 335, 358–360, 1988). Membranes were incubated in a final volume of 1 ml for 30 min at 30° C. with 0.2–1 nM [$^3$H]8-OH-DPAT, in absence or presence of competing drugs; non-specific binding was determined in the presence of 10 mM 5-HT. The incubation was stopped by addition of ice-cold Tris-HCl buffer and rapid filtration through 0.2% polyethyleneimine pretreated Whatman GF/B or Schleicher & Schuell GF52 filters.

B. Results

As shown in Table 2, the compounds of the present invention have a high affinity for serotonergic 5-HT$_{1A}$ receptors. These results show that the receptor has a role in the action exerted by the compounds of the invention on the bladder.

TABLE 2

Binding affinity for the 5-HT$_{1A}$ receptor
Data are expressed as Ki (nM).

| Compound | Ki (nM) |
|---|---|
| Compound A | 0.39 |
| Ex. 1 | 0.86 |
| Ex. 2 | 0.89 |

TABLE 2-continued

Binding affinity for the 5-HT$_{1A}$ receptor
Data are expressed as Ki (nM).

| Compound | Ki (nM) |
|---|---|
| Ex. 3 | 1.51 |
| Ex. 4 | 0.31 |
| Ex. 6 | 14.30 |
| Ex. 7 | 8.15 |
| Ex. 10 | 0.45 |
| Ex. 14 | 0.12 |

What is claimed is:

1. A compound of the formula:

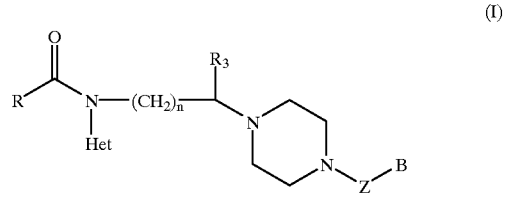

(I)

wherein n is 1 or 2,

Het is a pyridine radical,

R is a cycloalkyl or a monocyclic heteroaryl radical, wherein the monocyclic heteroaryl radical is an aromatic radical consisting from 5 to 6 ring atoms, and one or two of said ring atoms is a member selected from the group consisting of nitrogen, oxygen and sulfur, $R_3$ is a hydrogen atom or a lower alkyl group, Z is a —$CH_2$—, wherein B is selected from the group consisting of a heteroaryl radical and a substituted aryl radical, wherein said substituted aryl radical is represented the following formula:

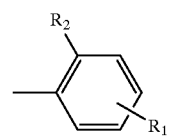

wherein $R_1$ is a single substituent selected from the group consisting of alkoxy, halogen, nitro, amino, acylamino, alkylamino, and alkylsulfonylamino, and $R_2$ is selected from the group consisting of an alkoxy, polyfluoroalkoxy, cyano, halogen and aminocarbonyl radical, and wherein said heteroaryl radical is selected from the group consisting of a monocyclic aromatic radical consisting from 5 to 6 ring atoms, wherein one or more of said ring atoms are selected from the group consisting of nitrogen, oxygen, and sulfur, and wherein said acylamino is selected from the group consisting of acetylamino, pivaloylamino, butanoylamino, phenylacetylamino, and formylamino, and enantiomers, diastereomers, N-oxides, crystalline forms, hydrates, and pharmaceutically acceptable salts thereof.

2. A compound of claim 1, wherein n is 1, R is cylohexyl, Het is 2-pyridyl, $R_3$ is hydrogen, $R_1$ is a single substituent selected from the group consisting of hydrogen, alkoxy, halogen, nitro, amino, acylamino, and alkylsulfonylamino and $R_2$ is selected from the group consisting of an alkoxy, polyfluoroalkoxy, cyano, halogen and aminocarbonyl radical.

3. A compound of claim 2 selected from the group consisting of:
1-[N-cyclohexylcarbonyl-N-(2-pyridyl)-2-aminoethyl]-4-(2-bromo-5-methoxybenzyl)-piperazine and
1-[N-cyclohexylcarbonyl-N-(2-pyridyl)-2-aminoethyl]-4-(2, 5-dichlorobenzyl)piperazine.

4. A pharmaceutical composition comprising a compound of claim 1 and a pharmaceutically acceptable diluent or carrier.

5. A method for treating neuromuscular dysfunction of the lower urinary tract in a mammal in need of such treatment, said method comprising administering to said mammal an effective amount for treating said dysfunction of a compound of the formula:

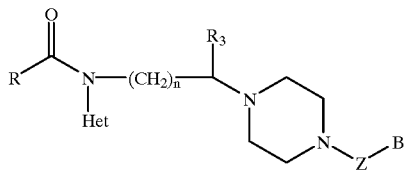

(I)

wherein
n is 1 or 2,
Het is a pyridine radical,
R is a cycloalkyl or a monocyclic heteroaryl radical,
wherein the monocyclic heteroaryl radical is an aromatic radical consisting from 5 to 6 ring atoms, and one or two of said ring atoms is a member selected from the group consisting of nitrogen, oxygen and sulfur,
$R_3$ is a hydrogen atom or a lower alkyl group,
Z is a —$CH_2$—,
wherein B is selected from the group consisting of a heteroaryl radical, an unsubstituted aryl radical, and a substituted aryl radical, wherein said substituted aryl radical is represented by the following formula:

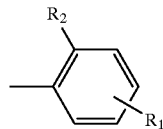

wherein $R_1$ is a single substituent selected from the group consisting of alkoxy, halogen, nitro, amino, acylamino, alkylamino, dialyklamino and alkylsulfonylamino, and $R_2$ is selected from the group consisting of an alkoxy, polyfluoroalkoxy, cyano, halogen and aminocarbonyl radical, and
wherein said heteroaryl radical is selected from the group consisting of a mono or a bicyclic aromatic radical consisting from 5 to 12 ring atoms, wherein one or more of said ring atoms are selected from the group consisting of nitrogen, oxygen, and sulfur;
and wherein said acylamino is selected from the group consisting of acetylamino, pivaloylamino, butanoylamino, phenylacetylamino, and formylamino; and enantiomers, diastereomers, N-oxides, crystalline forms, hydrates, and pharmaceutically acceptable salts thereof.

6. The method of claim 5, wherein said compound is selected from the group consisting of:
1-[N-cyclohexylcarbonyl-N-(2-pyridyl)-2-aminoethyl]-4-(2-bromo-5-methoxybenzyl) piperazine;
1-[N-cyclohexylcarbonyl-N-(2-pyridyl)-2-aminoethyl]4-(2, 5-dichlorobenzyl)piperazine; and
1-[N-cyclohexylcarbonyl-N-(2-pyridyl)-2-aminoethyl]-4-benzylpiperazine.

7. The method of claim 5, wherein said administration is effective for ameliorating at least one of urinary urgency, increased urinary frequency, incontinence, urine leakage, enuresis, dysuria, urinary hesitancy, and difficulty in bladder emptying in said mammal.

8. A method for treating neuromuscular dysfunction of the lower urinary tract in a mammal in need of such treatment, said method comprising administering to said mammal an effective amount of a compound of claim 6 for ameliorating at least one of urinary urgency, increased urinary frequency, incontinence, urine leakage, enuresis, dysuria, urinary hesitancy, and difficulty in bladder emptying in said mammal.

9. The method of claim 5, wherein said administering is achieved using a route selected from the group consisting of oral, enteral, intravenous, intramuscular, subcutaneous, transmucosal, transdermal, and by-inhalation routes.

10. The method of claim 9, wherein said compound is administered to said mammal in an amount of between about 0.01 and 25 mg/kg/day.

11. The method of claim 9, wherein said amount is between about 0.2 and about 5 mg/kg/day.

12. The method of claim 9, wherein the amount of said compound is between about 50 and 400 mg/day.

13. The method of claim 9, wherein the amount of said compound is about 200 mg/day.

14. The method of claim 8, wherein said administering is achieved using a route selected from the group consisting of oral and transdermal routes.

15. The method of claim 14, wherein the amount of said compound is between about 0.1 and 10 mg/kg/day.

16. A pharmaceutical composition comprising a compound of claim 3 and a pharmaceutically acceptable diluent or carrier.

17. The pharmaceutical composition of claim 16 which comprises at least one excipient selected from the group consisting of lubricants, plasticizers, colorants, absorption enhancers, and bactericides.

* * * * *